US012564468B2

(12) United States Patent
Meadows et al.

(10) Patent No.: US 12,564,468 B2
(45) Date of Patent: Mar. 3, 2026

(54) IMPLANT LOAD FEEDBACK APPARATUS

(71) Applicant: GLOBUS MEDICAL, INC., Audubon, PA (US)

(72) Inventors: Nicholas Meadows, Langhorne, PA (US); Philip Levins, Conshohocken, PA (US); Timothy James, Hatboro, PA (US); George Yacoub, Lansdale, PA (US); Patrick Murray, Collegeville, PA (US)

(73) Assignee: Globus Medical Inc., Audubon, PA (US)

( * ) Notice: Subject to any disclaimer, the term of this patent is extended or adjusted under 35 U.S.C. 154(b) by 117 days.

(21) Appl. No.: 18/512,362

(22) Filed: Nov. 17, 2023

(65) Prior Publication Data

US 2025/0160992 A1 May 22, 2025

(51) Int. Cl.
| | |
|---|---|
| *A61B 90/00* | (2016.01) |
| *A61B 17/56* | (2006.01) |
| *A61B 17/70* | (2006.01) |
| *A61F 2/44* | (2006.01) |
| *A61F 2/46* | (2006.01) |

(52) U.S. Cl.
CPC .......... *A61B 90/06* (2016.02); *A61B 17/7082* (2013.01); *A61F 2/442* (2013.01); *A61F 2/4455* (2013.01); *A61F 2/4611* (2013.01); *A61B 2017/564* (2013.01); *A61B 2090/064* (2016.02); *A61B 2090/3937* (2016.02); *A61F 2002/4666* (2013.01)

(58) Field of Classification Search
CPC ........... A61F 2002/4666; A61F 2/4611; A61B 17/8875; A61B 2090/031; A61B 2090/066; A61B 2562/0266; B25B 23/1425
See application file for complete search history.

(56) References Cited

U.S. PATENT DOCUMENTS

| | | | |
|---|---|---|---|
| 1,596,687 A | 8/1926 | Roach | |
| 4,062,203 A | 12/1977 | Leonard et al. | |
| 4,262,501 A | 4/1981 | Vaughn et al. | |
| 5,433,665 A * | 7/1995 | Beaty ................... | A61C 8/0089 464/37 |
| 6,425,920 B1 * | 7/2002 | Hamada ................ | A61L 27/365 623/17.16 |
| 7,197,968 B2 | 4/2007 | Bubel | |
| 7,406,900 B1 | 8/2008 | Hsieh | |
| 8,485,075 B1 * | 7/2013 | Gauthier ............ | A61B 17/8875 81/479 |
| 8,602,899 B2 | 12/2013 | You | |

(Continued)

FOREIGN PATENT DOCUMENTS

| | | |
|---|---|---|
| CN | 102019604 A | 4/2011 |
| CN | 104802124 A | 7/2015 |

(Continued)

*Primary Examiner* — David W Bates

(57) ABSTRACT

Various implementations include apparatuses for providing feedback on an implant. In a particular implementation, an apparatus includes: a transport device for loading the implant in a patient; an actuator coupled with the transport device for actuating movement of the implant in the patient; and a load indicator coupled with at least one of the actuator or the transport device, the load indicator providing feedback indicative of a load on at least one of the implant or a body part of the patient.

14 Claims, 24 Drawing Sheets

(56) References Cited

U.S. PATENT DOCUMENTS

| | | | |
|---|---|---|---|
| 9,162,350 B2 | 10/2015 | Nino et al. | |
| 9,409,285 B2 | 8/2016 | Ivinson et al. | |
| 11,027,402 B2 | 6/2021 | Chuang | |
| 11,203,102 B2 | 12/2021 | Nino et al. | |
| 11,253,983 B2* | 2/2022 | Chiang | B25B 23/141 |
| 11,518,010 B2 | 12/2022 | Jenkins et al. | |
| 11,618,138 B2 | 4/2023 | Jenkins | |
| 2004/0220582 A1* | 11/2004 | Keller | A61F 2/4611 |
| | | | 606/99 |
| 2007/0050030 A1* | 3/2007 | Kim | A61F 2/4611 |
| | | | 623/17.11 |
| 2008/0065222 A1* | 3/2008 | Hamada | A61F 2/4657 |
| | | | 623/17.11 |
| 2013/0079792 A1* | 3/2013 | Stein | A61F 2/4611 |
| | | | 606/102 |
| 2013/0317372 A1* | 11/2013 | Eberle | A61B 5/6851 |
| | | | 600/478 |
| 2015/0282797 A1* | 10/2015 | O'Neil | A61B 5/1076 |
| | | | 606/279 |
| 2017/0095343 A1* | 4/2017 | Aryan | A61B 17/025 |
| 2019/0314962 A1 | 10/2019 | King et al. | |
| 2020/0222266 A1* | 7/2020 | Gordon | A61H 3/008 |
| 2021/0031341 A1 | 2/2021 | Chang et al. | |
| 2023/0141374 A1 | 5/2023 | Elsawah et al. | |

FOREIGN PATENT DOCUMENTS

| | | |
|---|---|---|
| CN | 211094637 U | 7/2020 |
| JP | 2022101231 A | 7/2022 |
| WO | 2007034044 A1 | 3/2007 |
| WO | 2015153376 A1 | 10/2015 |
| WO | 2017062290 A1 | 4/2017 |
| WO | 2021020895 A1 | 2/2021 |
| WO | 2023280337 A1 | 1/2023 |

* cited by examiner

IMPLANT LOAD FEEDBACK APPARATUS

TECHNICAL FIELD

This disclosure generally relates to the field of spinal surgery and spinal implants. More particularly, the disclosure relates to apparatuses, systems, and approaches for providing feedback on a spinal implant procedure.

BACKGROUND

The spine is the axis of the skeleton on which all of the body parts "hang." In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centers of adjacent vertebrae are supported by intervertebral discs. The intervertebral discs and/or vertebral bodies of the spine may be displaced or damaged due to trauma, disease, degenerative defects, or wear over an extended period of time. One result of this displacement or damage to a spinal disc or vertebral body may be chronic back pain. In many cases, to alleviate back pain from degenerated or herniated discs, the disc is removed along with all or part of at least one neighboring vertebra and is replaced by an implant that promotes fusion of the remaining bony anatomy.

However, the success or failure of spinal fusion may depend upon several factors. For instance, the spacer or implant or cage used to fill the space left by the removed disc and bony anatomy must be sufficiently strong to support the spine under a wide range of loading conditions. Additionally, the material used for the spacer should be biocompatible material and should have a configuration that promotes bony ingrowth. Further, the spacer should also be configured so that it is likely to remain in place once it has been positioned in the spine by the surgeon.

SUMMARY

The needs above, as well as others, are addressed by embodiments of apparatuses for providing feedback on implants, as well as systems for providing implant feedback, and related methods described in this disclosure. All examples and features mentioned below can be combined in any technically possible way.

Various implementations include apparatuses for providing feedback on an implant. In a particular implementation, an apparatus includes: a transport device for loading the implant in a patient; an actuator coupled with the transport device for actuating movement of the implant in the patient; and a load indicator coupled with at least one of the actuator or the transport device, the load indicator providing feedback indicative of a load on at least one of the implant or a body part of the patient.

In particular aspects, the system further includes an optical feedback system for detecting indicators of a load on the implant and/or the body part of the patient.

In further particular aspects, a method of performing an anterior lumbar interbody fusion (ALIF) or a lateral lumbar interbody fusion (LLIF) procedure uses the apparatus.

Implementations may include one of the following features, or any combination thereof.

In certain examples, the transport device comprises an intervertebral body (IB) transport device.

In particular implementations, the implant comprises an intervertebral spacer for occupying an intervertebral disc space in a spinal region of the patient.

In some examples, the intervertebral body (IB) transport device comprises: a guide body; a distractor coupled with the guide body for transporting the intervertebral spacer relative to the intervertebral disc space; and set of distraction arms for positioning the intervertebral spacer in the intervertebral disc space.

In certain aspects, the actuator comprises a driver coupled with a distal end of the distractor for causing movement of the distractor relative to the guide body.

In some cases, the driver is directly coupled with the load indicator, and the driver comprises a rotatable member. In some examples, the rotatable member includes a threaded actuator input handle that mates with a receiver in the guide body. In certain of these cases, the guide body is internally threaded, such that the threaded actuator input handle translates as it rotates relative to the guide body, thereby causing translation of the distractor.

In certain cases, the set of distraction arms can be configured to expand to engage one or more vertebra adjacent the intervertebral disc space in response to rotation of the rotatable member, and in response to rotation of the rotatable member after the distraction arms engage the one or more vertebra adjacent the intervertebral disc space, the distractor transports the intervertebral spacer relative to the intervertebral disc space.

In particular implementations, the load indicator includes a housing containing a communications device for transmitting the feedback indicative of the load to a surgical management system.

In some cases, the housing includes a set of markers configured to provide visual feedback of an amount of rotation of the driver, and the housing is configured to be hermetically sealed and includes a rechargeable power source.

In certain aspects, the load indicator is disposable and configured for one-time use.

In particular implementations, the apparatus further includes a release mechanism for releasing the implant from the transport device, wherein the release mechanism is adjustable independently of the actuator.

In some cases, the load indicator comprises at least one of: a load cell, a torque cell, an active marker cell, an optical indicator cell, a proximity indicator cell, or a strain gauge.

In certain aspects, the apparatus further includes a release mechanism for releasing the implant from the transport device, wherein the release mechanism is adjustable independently of the actuator.

In certain implementations, the transport device comprises a screwdriver for loading a screw into the body part of a patient or into an implant in a patient, the screwdriver having: a rotatable member for driving the screw; a shaft extending from the rotatable member; and the load indicator coupled with at least one of the rotatable member or the shaft. In some examples, the rotatable member includes a grip or a handle.

In some cases, the load indicator is axially aligned with, and located between, the rotatable member and the shaft.

In certain aspects, the load indicator is housed within the rotatable member.

In particular implementations, the load indicator includes at least one of a torque cell, a strain gauge, or an end effector.

In some aspects, the load indicator comprises: a housing containing the strain gauge; and a drive shaft extending through the housing, the drive shaft having a recess, where the strain gauge is located in the recess in the drive shaft and is configured to indicate a load on the drive shaft.

In particular implementations, the load indicator comprises a torque cell including a spring-loaded clutch mechanism.

In certain cases, the torque cell comprises at least one of: a) a set of optical markers, wherein relative location of the set of optical markers provides the feedback indicative of the load, b) an internal force sensor, or c) an internal proximity sensor.

In certain examples, optical markers can be tracked by a medical professional such as a surgeon or surgical technician and/or by an optical feedback system such as a camera system.

In particular aspects, the apparatus further includes at least one coupler integral with the load indicator, the at least one coupler enabling a snap-to-couple or twist-to-couple connection with one or both of the transport device or the actuator.

Two or more features described in this disclosure, including those described in this summary section, may be combined to form implementations not specifically described herein.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The details of one or more implementations are set forth in the accompanying drawings and the description below. Other features, objects and benefits will be apparent from the description and drawings, and from the claims.

Figure 1:
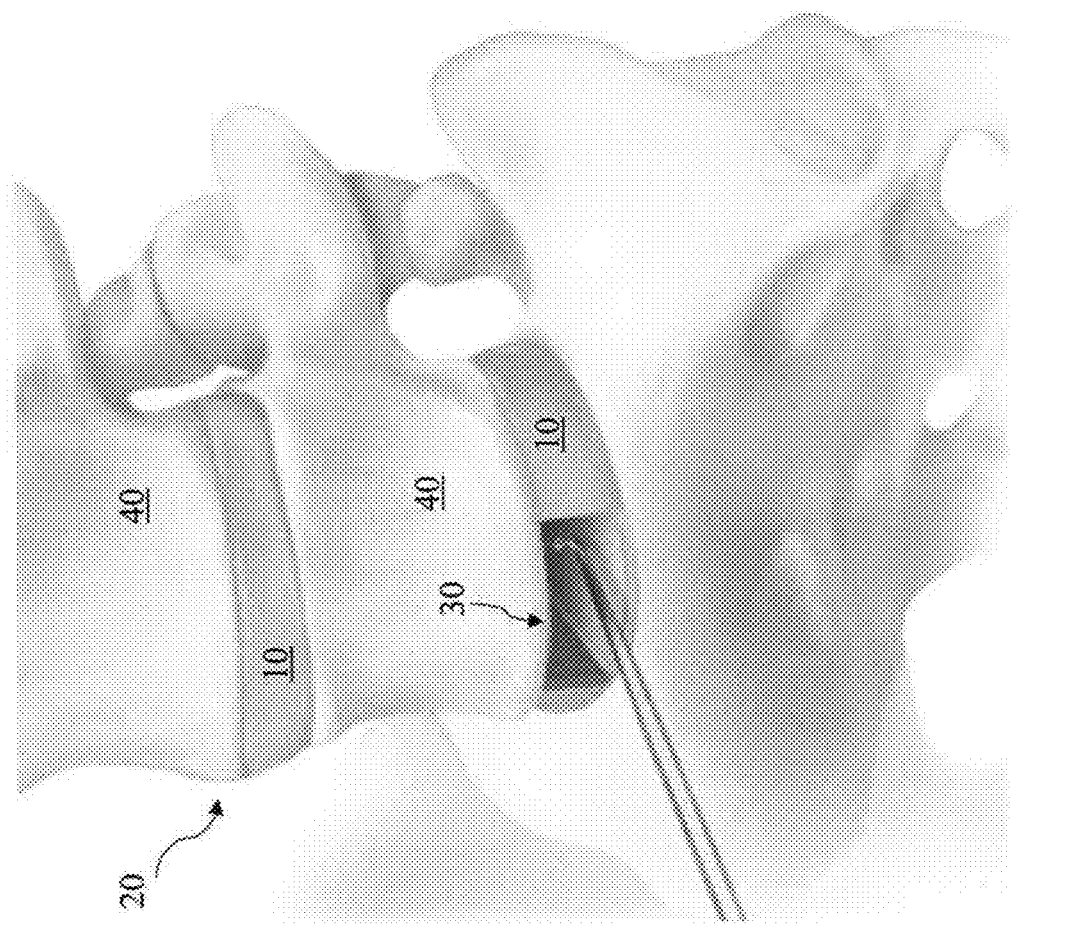
FIG. 1 shows a perspective view of a portion of a spine undergoing an intervertebral fusion procedure according to various implementations.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

Various example embodiments of apparatuses, systems, and approaches for providing feedback on a spinal implant procedure are described herein. In the interest of clarity, not all features of an actual implementation are necessarily described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The apparatuses and related systems and methods described herein boast a variety of inventive features and components that warrant patent protection, both individually and in combination.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

As disclosed herein, the term fastener is used interchangeably with, and is considered equivalent to and synonymous with the terms: bone fastener, bone anchor, fixation screw, spinal fixation screw, bone screw, and pedicle screw. The term driver is used interchangeably with, and is considered equivalent to and synonymous with a screw driver, or any device that drives insertion of a fastener as would be understood by one skilled in the art. Use of the term proximal refers to the direction away from attachment of an element to the subject, shown in FIG. 5 as direction P, while use of the term distal refers to the direction opposite the proximal direction and toward attachment of an element to the subject, shown in FIG. 5 as direction D.

This disclosure provides, at least in part, an apparatus for providing feedback on an implant, related systems, and methods that beneficially incorporate a load indicator to enhance efficacy of implant procedures, as well as mitigate opportunity for operator (e.g., surgeon) error in performing such procedures. In certain cases, the implant procedure includes an anterior lumbar interbody fusion (ALIF) or a lateral lumbar interbody fusion (LLIF) procedure. The various disclosed implementations can improve patient outcomes when compared with conventional implant procedures. The disclosed implementations can provide real-time and/or post-operative feedback on implant procedures, enhancing both current procedural outcomes as well as future surgical outcomes.

Commonly labeled components in the FIGURES are considered to be substantially equivalent components for the purposes of illustration, and redundant discussion of those components is omitted for clarity.

As noted herein, the success or failure of spinal fusion may depend upon several factors. For example, the spacer (also called an intervertebral implant, or an interbody cage) should be configured so that it is likely to remain in place once it has been positioned in the spine by the surgeon. Precisely positioning and securing the spacer can reduce the risk of potential complications such as fracture of or damage to vertebral endplates, implant misplacement, nerve or tissue injury, implant subsidence, and implant expulsion.

Figure 2:
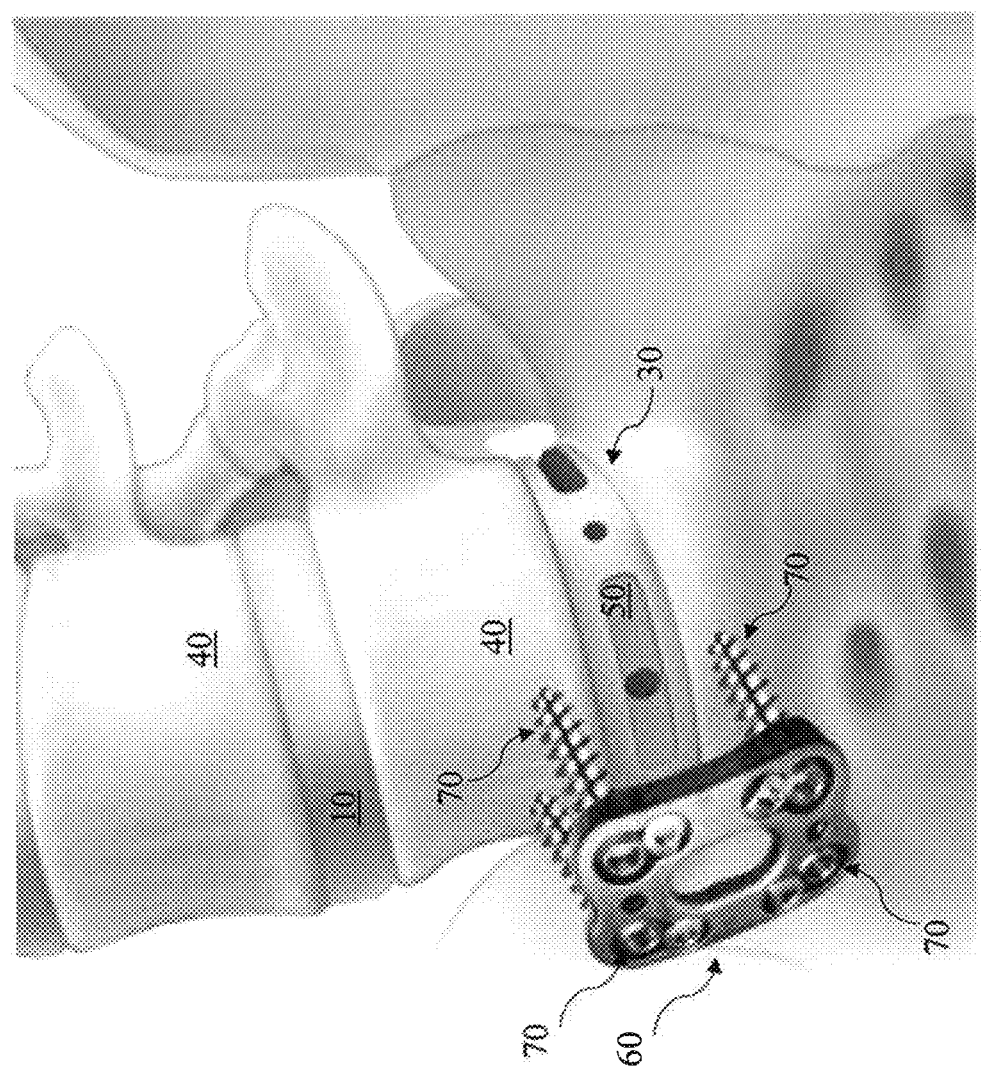
FIG. 2 shows a perspective view of a portion of a spine undergoing an intervertebral fusion procedure according to various implementations.
Figure 3:
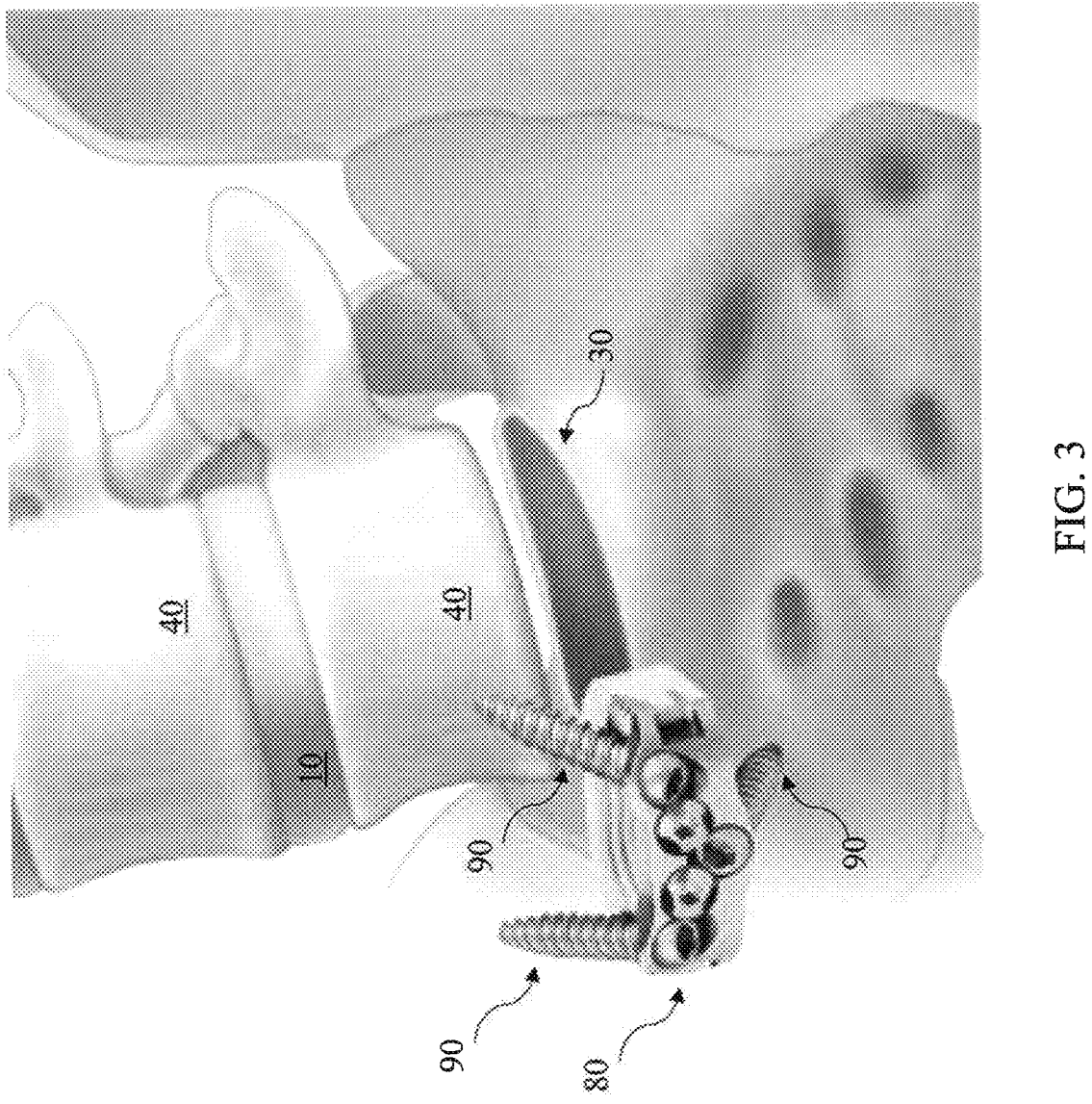
FIG. 3 shows a perspective view of a portion of a spine undergoing an intervertebral fusion procedure according to various implementations.

Placing a spacer (or implant, or cage) during a spinal surgery such as an ALIF or LLIF procedure involves several steps that can vary by procedure. Typically, a spacer is positioned in the disc space aligned with prepared endplates. In conventional procedures, an instrument such as a mallet is used to carefully impact the spacer into place, with the position and alignment of the spacer confirmed using imaging such as fluoroscopy. Securing the spacer can be performed with a separate plate and fasteners (e.g., screws), or the spacer can include an integrated plate-spacer that is configured to receive fasteners. FIG. 1 is a schematic illustration of a process in an ALIF procedure including removing an unhealthy portion of a disc 10 from a patient's spinal region 20, e.g., creating space 30 adjacent to vertebra 40. FIG. 2 illustrates placement of a spacer (or, implant, or cage) 50 in the space 30, and subsequent placement of a plate 60 and fasteners 70 (e.g., screws) to hold the vertebral body or bodies (e.g., vertebrae) 40 in place while fusion occurs. FIG. 3 illustrates a distinct spacer 80 that includes integrated fasteners 90 for holding the vertebrae 40 in place while fusion occurs. Various spacer types and sizes can be inserted and secured according to implementations described herein, such as those illustrated in U.S. Pat. No. 11,723,779 ("Intervertebral Spinal Implant," issued Aug. 15,

6

Figure 4:
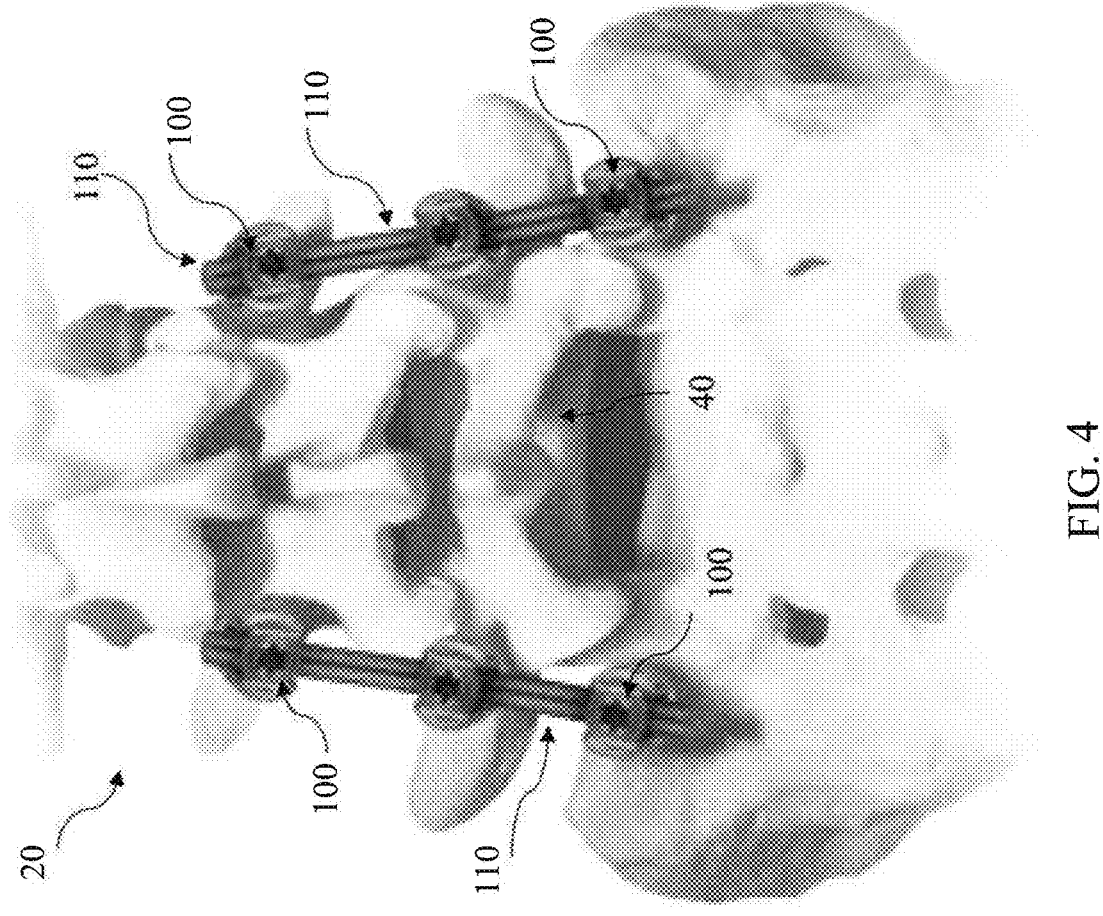
FIG. 4 shows a perspective view of a portion of a spine undergoing an intervertebral fusion procedure according to various implementations.

2023), the entire contents of which are incorporated by reference herein. In some cases, following the anterior procedure illustrated in FIGS. 1-3, posterior stabilization is used to aid in holding the vertebral body 40 in place. Posterior stabilization includes entering through the back of the body to place fasteners (e.g., screws) and rods to further stabilize vertebral body 40 during fusion. Similar to an ALIF procedure, an LLIF procedure involves using a spacer and plate, or integrated spacer/plate to hold vertebrae 40 in place while fusion occurs. As with an ALIF procedure or related posterior stabilization, and as illustrated schematically in FIG. 4, screws 100 may be inserted into the left and right sides of the vertebral body 40 to be fused, such screws 100 being connected by rods 110 that stabilize the spine on each side during fusion. In conventional approaches, it can be difficult for medical professionals (e.g., surgeons and technicians) to assess the load applied on implanted devices such as spacers 50, 80, or fasteners (e.g., screws) 70, 90, 100, etc., as well as on the patient's bone or other tissue during a procedure, e.g., during an ALIF or LLIF procedure. As described herein, various implementations enable enhanced load feedback on implants and body parts of patients when compared with conventional approaches.

Figure 5:
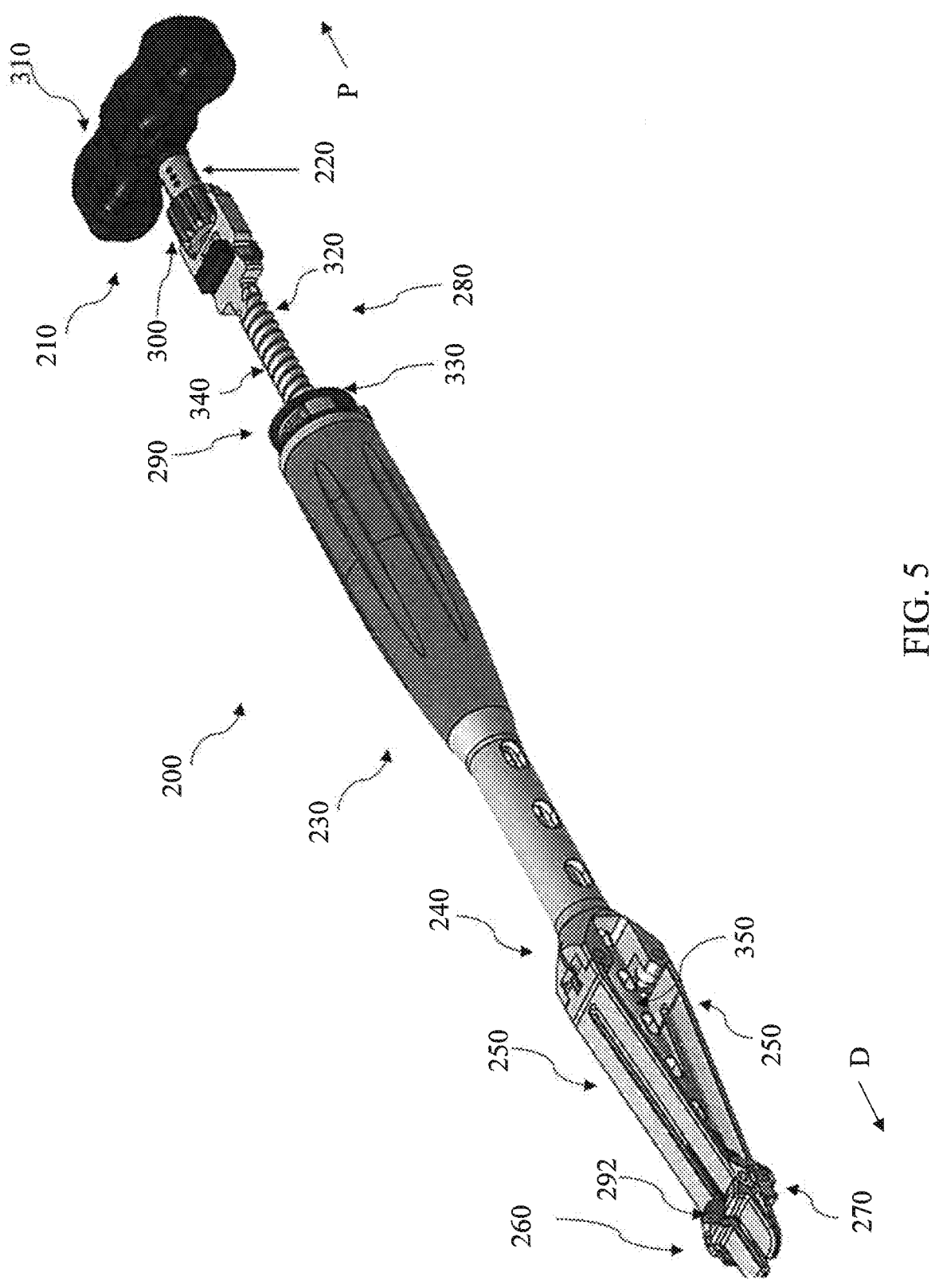
FIG. 5 shows a perspective view of a transport device according to various implementations.

As shown schematically in FIGS. 5-8, in certain implementations, an intervertebral body (IB) transport device 200 is used to transport (e.g., load) an implant such as a spacer (e.g., spacer 50, 80) into a patient. In certain cases, the IB transport device 200 includes an inserter/distractor device such as an ALIF inserter/distractor. In particular cases, as shown in FIG. 5, the IB transport device 200 includes an actuator 210 for actuating movement of the implant (e.g., spacer 50, 80) in the patient. In a particular example, the IB transport device 200 further includes a load indicator 220 coupled with the actuator 210 or another portion of the IB transport device 200 for providing feedback indicative of a load on the implant (e.g., 50, 80) or a body part of the patient (e.g., vertebral body 40).

Figure 6:
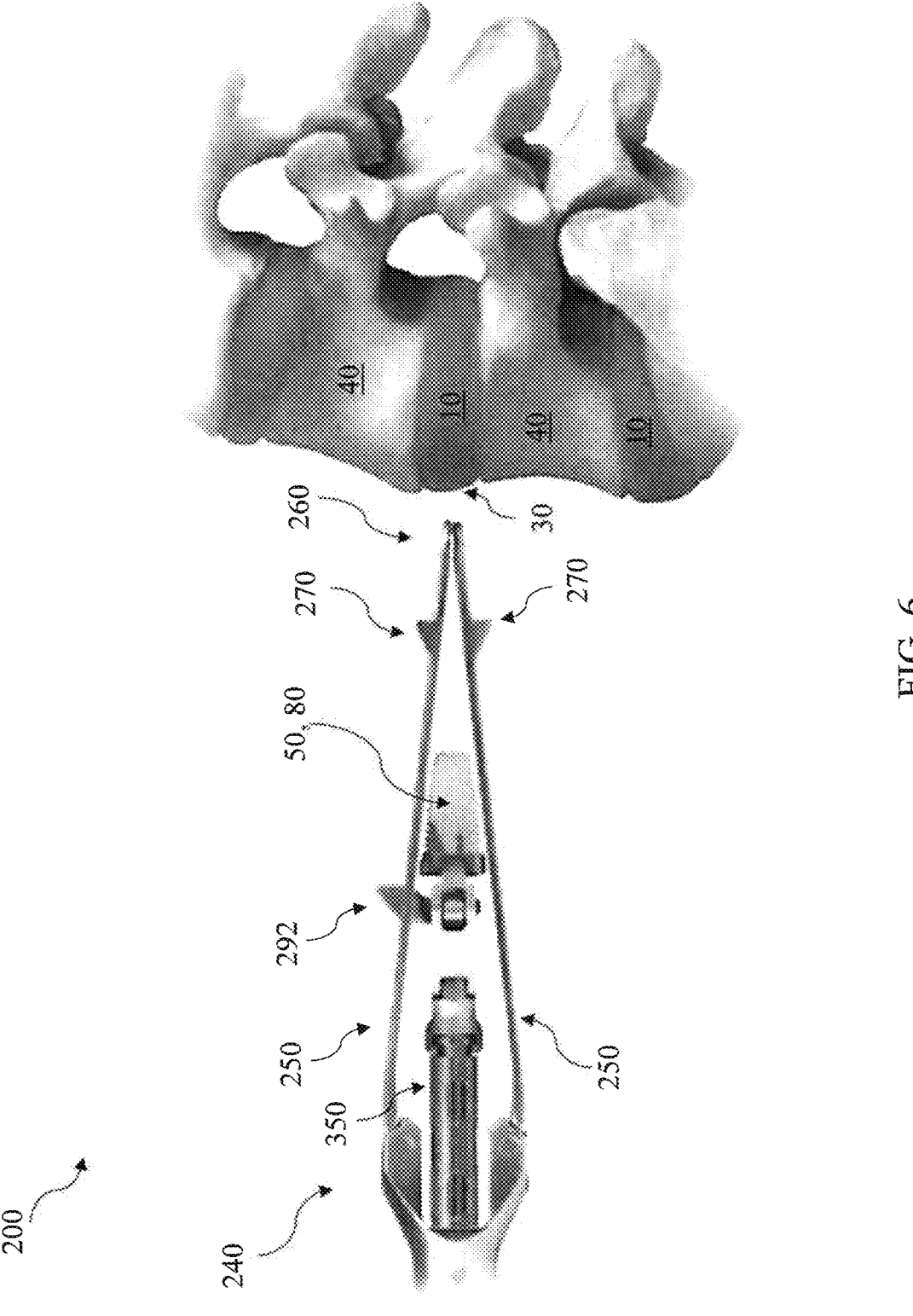
FIG. 6 illustrates a perspective view of a transport device during a step of an intervertebral fusion procedure according to various implementations.
Figure 7:
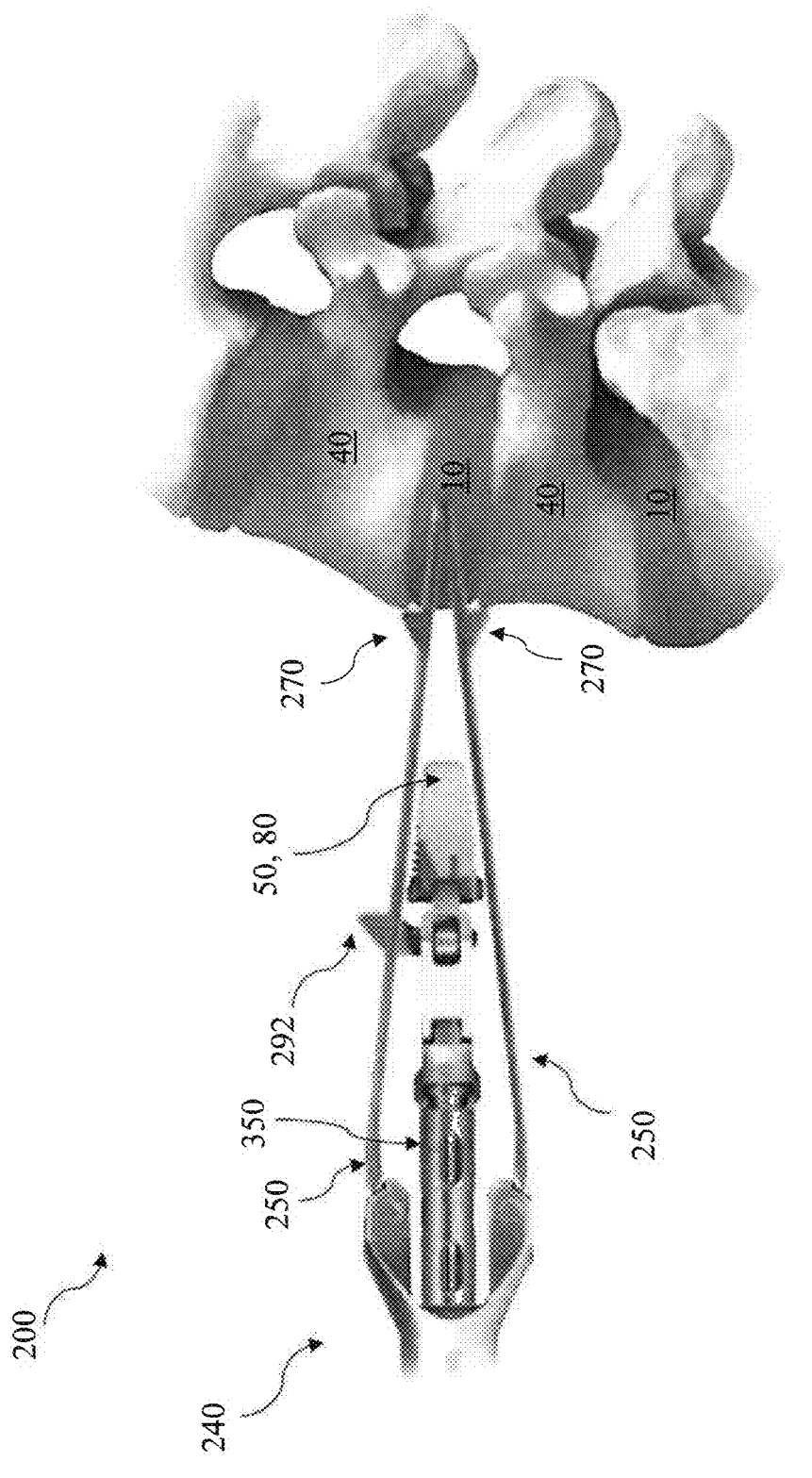
FIG. 7 illustrates a perspective view of a transport device during a step of an intervertebral fusion procedure according to various implementations.
Figure 8:
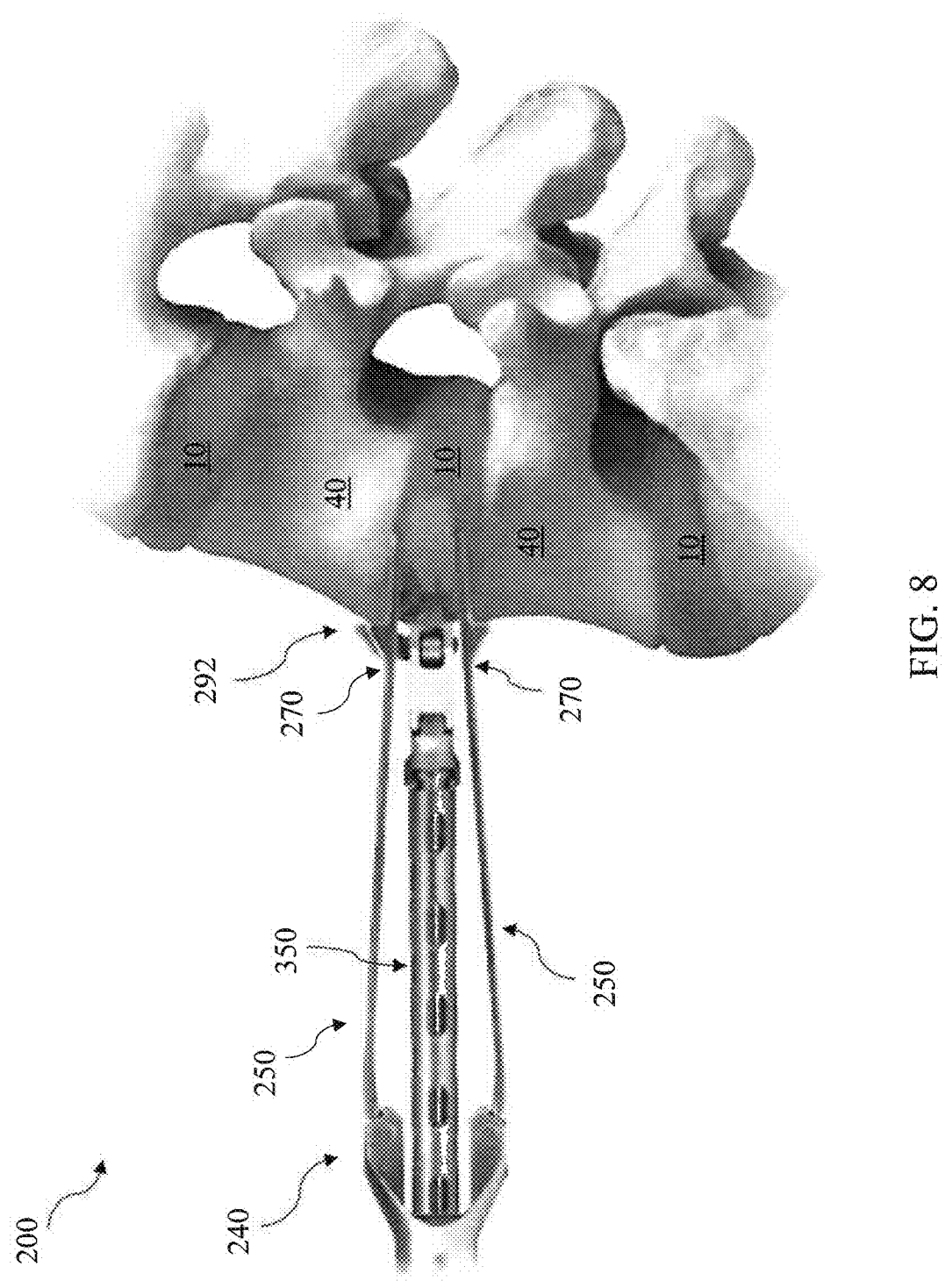
FIG. 8 illustrates a perspective view of a transport device during a step of an intervertebral fusion procedure according to various implementations.

In the particular example in FIGS. 5-8, the IB transport device 200 includes a guide body 230, and a distractor 240 coupled with the guide body 230 for transporting the implant (e.g., spacer 50, 80) relative to the intervertebral disc space 30. A set of distraction arms 250 are located at a distal end 260 of the distractor 240. The distraction arms 250 aid in positioning the spacer 50, 80 in the intervertebral disc space 30. In a particular example shown in FIGS. 6-8, the distraction arms 250 are inserted into the disc space 30 until depth stops 270 engage the anterior rim of the vertebral bodies 40 (FIGS. 7-8). After the depth stops 270 engage the anterior rim of the vertebral bodies 40, the actuator 210 can be used to actuate movement of the spacer 50, 80 via the distractor 240 (FIG. 8). In various implementations, as shown in FIGS. 6-8, the distractor 240 transports the spacer 50, 80, axially into the space 30. In the example in FIGS. 5-8, the actuator 210 can include a driver 280 coupled with a proximal end 290 of the distractor 240 for causing movement of the distractor 240 relative to the guide body 230. The distractor 240 can include an ejection prong 292 that is configured to engage with the vertebral body/bodies 40 once the spacer 50, 80 is fully inserted. Continuing to actuate the distractor 240 after the ejection prong 292 engages the vertebral body 40 can cause the distraction arms 250 to retract. Further, as shown in FIG. 5, the IB transport device 200 can include a release mechanism 300 for releasing the spacer 50, 80 from the distractor 240. In particular implementations, the release mechanism 300 is adjustable independently of the actuator 210. After releasing the spacer 50, 80, the transport device can be removed from the patient.

With particular attention to FIG. 5, in various implementations the driver 280 is directly coupled with the load indicator 220. In a particular example, the driver 280 includes a rotatable member 310 such as a handle or grip that enables an operator to rotate the driver 280. In a particular example, the rotatable member 310 includes an input handle coupled with a shaft (or, input shaft) 320 for mating with a receiver 330 in the guide body 230. In certain cases, the shaft 320 has a threaded external surface 340 that mates with a threaded internal surface (not shown) of the guide body 230. Rotation of shaft 320 causes translation of the driver 280 as the external threads 340 and internal threads of the guide body 230 interact. In a particular implementation, the distractor 240 includes a shaft (or, output shaft) 350 coupled with the guide body 230 and configured to translate in response to movement of shaft 320. In various implementations, shafts 320, 350 are connected with a rotatable coupler inside guide body 230, which enables shaft 350 to translate without rotation while shaft 320 translates and rotates. In additional cases, a rotation stop such as a set of complementary tabs and grooves are used to limit rotation of shaft 350 during translation. In any case, shaft 350 is coupled with input shaft 320 and is configured to translate in the proximal-distal direction as the input shaft 320 is rotated. As noted herein with respect to FIGS. 5-9, the set of distraction arms 250 are configured to expand to engage the vertebral body (or bodies) 40 adjacent the space 30 in response to rotation of the rotatable member 310. Further, in response to rotation of the rotatable member 310 after the distraction arms 250 engage the one or more vertebral bodies 40 adjacent the intervertebral disc space 30, the distractor 240 transports the intervertebral spacer 50, 80 relative to the intervertebral disc space 30.

Figure 10:
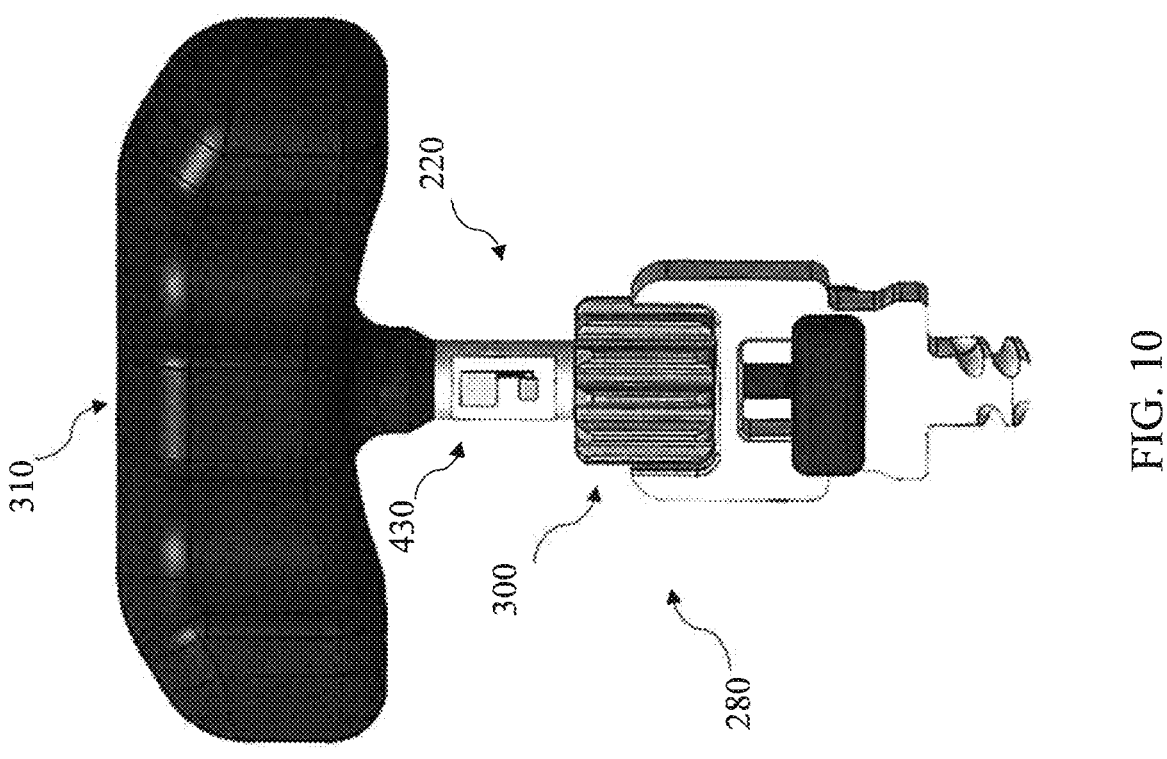
FIGS. 9 and 10 illustrate perspective views of a portion of the transport device in FIGS. 5-8, including a load indicator.
Figure 9:
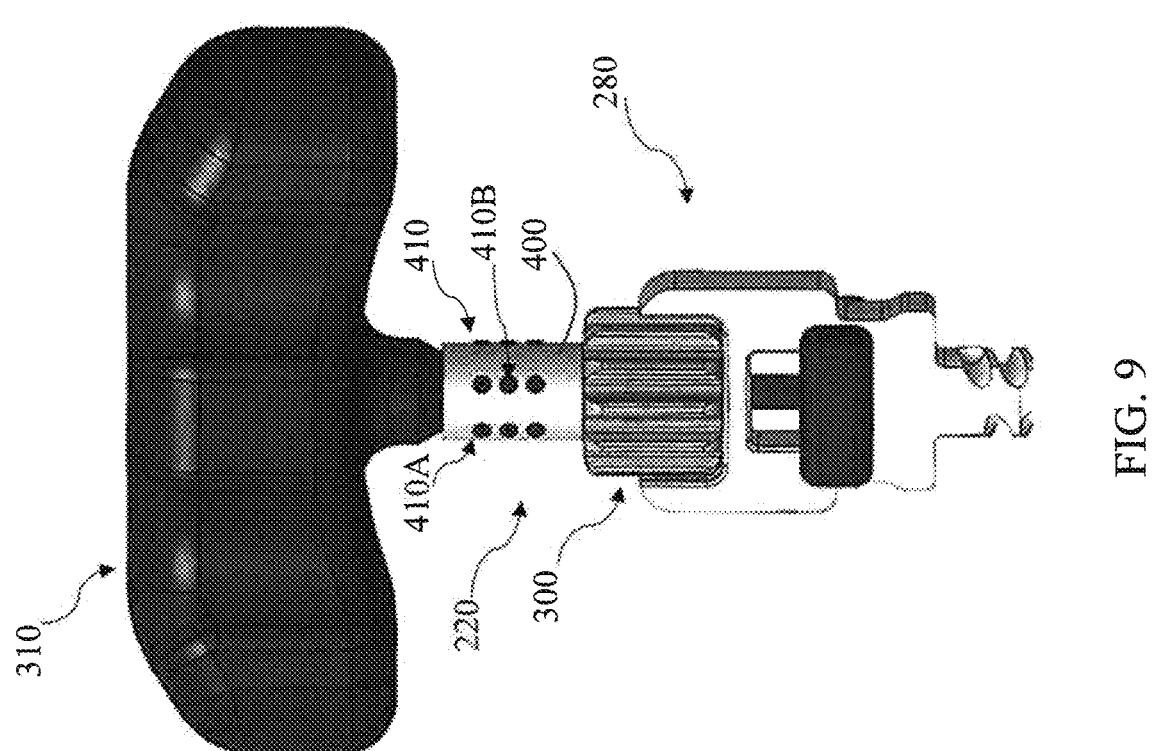

In particular implementations, as shown in FIGS. 5, 9, and 10, the driver 280 can be directly coupled with the load indicator 220. In certain cases, load indicator 220 includes a housing 400 (FIG. 9) containing a communications device for transmitting the feedback indicative of the load to a surgical management system, for example, a surgical management system such as disclosed in U.S. Pat. No. 11,083,527 ("Systems and Methods for Assisted Surgical Navigation," issued on Aug. 10, 2021), the entire contents of which are incorporated by reference herein.

Figure 34:
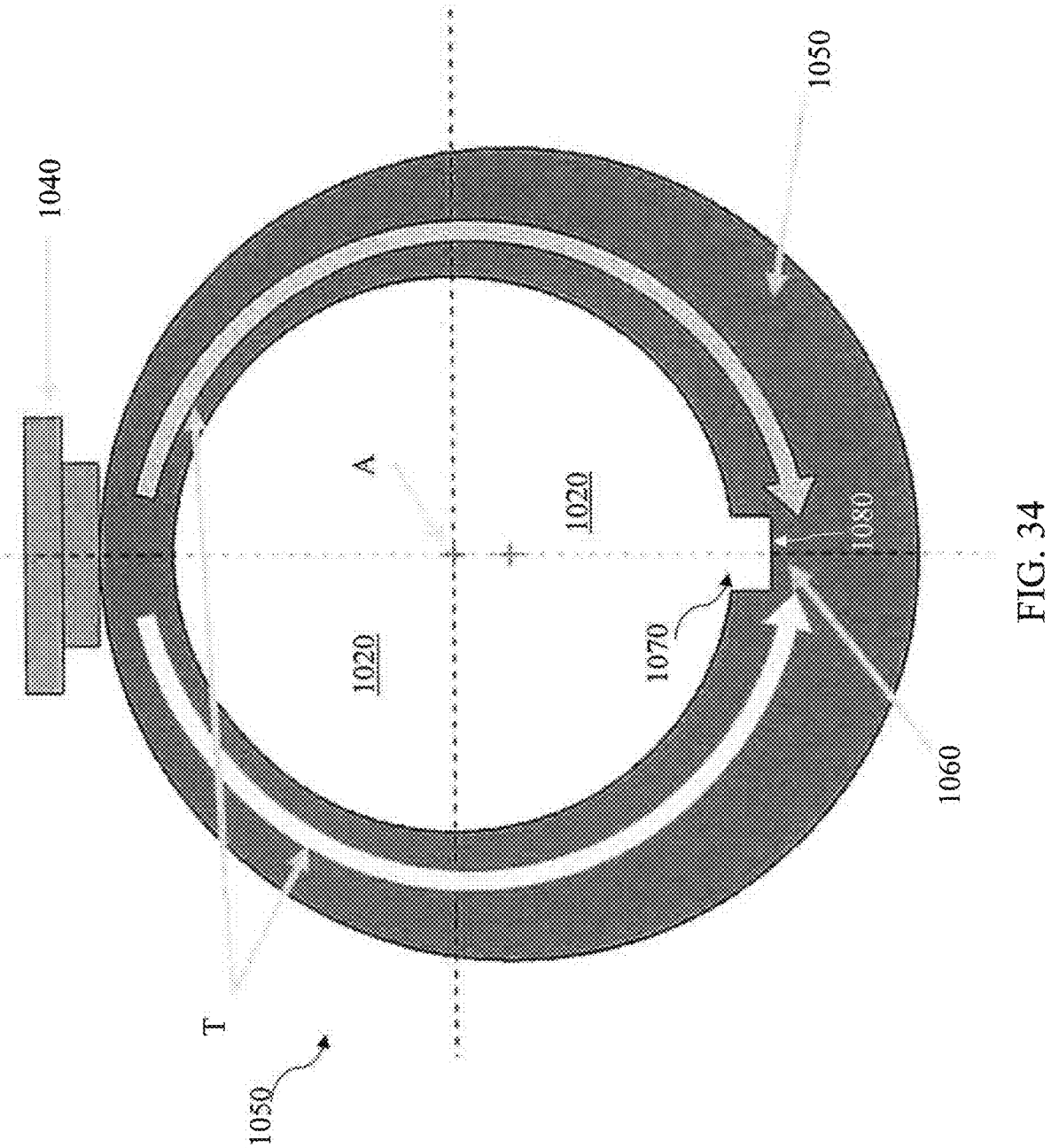
FIG. 34 shows an end effector from the robotic arm of FIG. 33 according to various implementations.

In particular implementations, such as illustrated in FIG. 9, the housing 400 includes a set of markers 410 configured to provide visual feedback on an amount of rotation of the driver 280. In certain cases, the markers 410 include color-coded or location-differentiating indicators that indicate an amount of rotation of the driver 280 from a baseline. For example, markers 410 can include distinct rows 410A, 410B, etc., that are arranged annularly relative to translation axis (A) (FIG. 34). In various implementations, the markers 410 are located on a fixed housing 400, such that as the driver 280 (e.g., handle 310) is rotated, a user can view the degree of rotation via the markers 410.

In various implementations, e.g., as shown in FIG. 10, the load indicator 220 can include an internal housing 430 that is contained within fixed housing 400. In certain examples, the internal housing 430 includes at least one of a color or design element that is visible through markers 410A, 410B, etc., to indicate an amount of rotation of the internal housing 430 relative to fixed housing 400.

In particular examples, the load indicator 220 includes a rechargeable power source such as a rechargeable battery. In certain of these cases, the load indicator 220 is hermetically sealed. In various example cases, the load indicator 220 can be configured for multiple uses, e.g., after sterilization. That is, the housing 430 can hermetically seal electronic components such as a load cell, torque cell, communications devices, etc., and enable sterilization and subsequent use of the load indicator 220 for additional patients. In other implementations, the load indicator 220 is not necessarily hermetically sealed. In such examples, the power source for the load indicator 220 is not necessarily rechargeable. In these cases, the load indicator 220 can include a disposable load indicator that is configured for one-time (single) use.

Figures 11, 12:
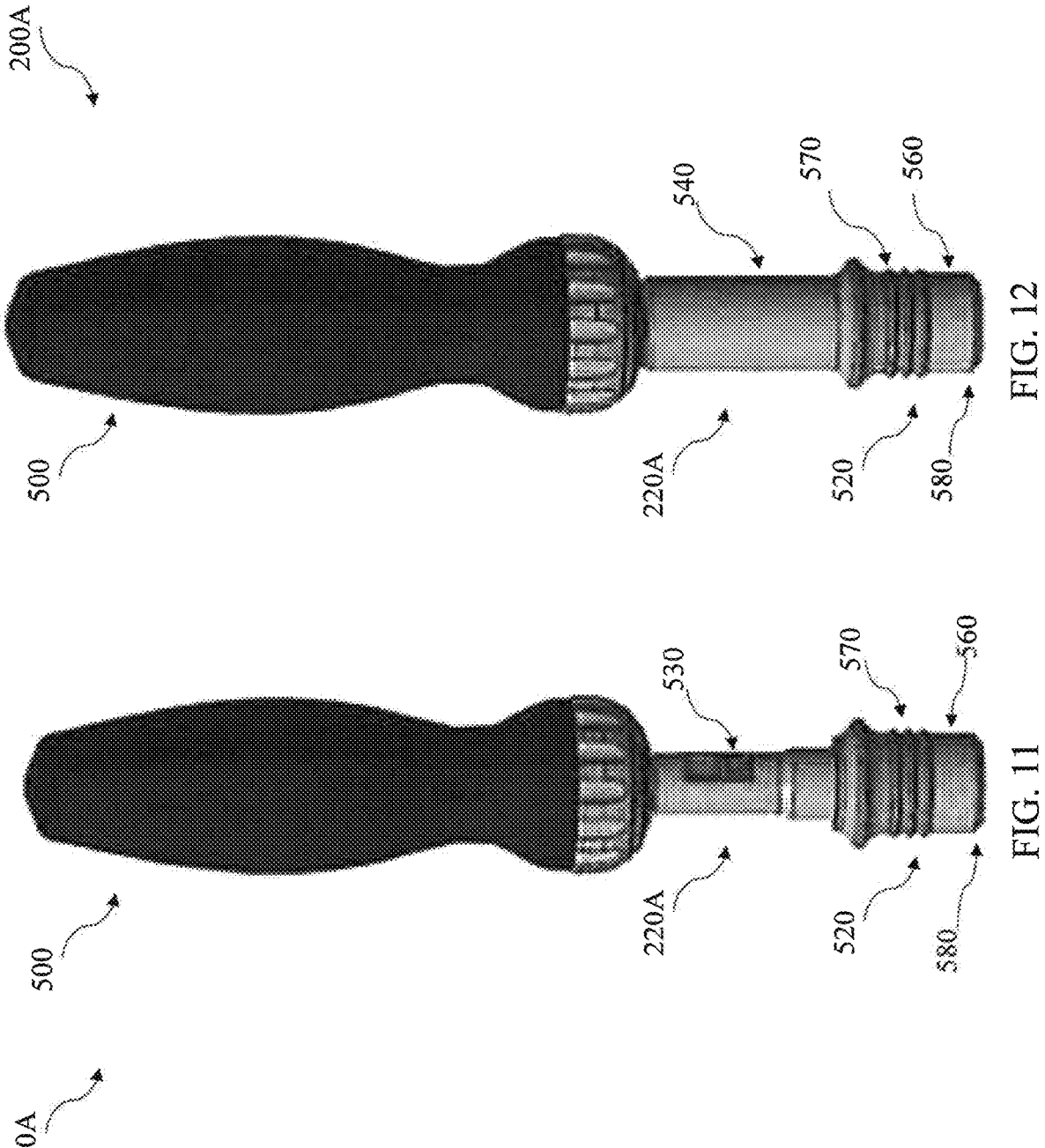
FIGS. 11 and 12 illustrate perspective views of a portion of a transport device including a load indicator according to various additional implementations.

While the example of an inserter/distractor type transport device 200 is shown and illustrated with respect to FIGS. 5-10, various additional types of transport devices 200 benefit from the disclosed implementations herein. For example, a screwdriver or reducer type transport device can benefit from the disclosed implementations, including for example, a load indicator 220. FIGS. 11 and 12 show a portion of another example transport device 200A, e.g., a screwdriver. It is understood that the description of load indicators relative to screwdrivers, reducers, or other surgical instruments can be equally applicable to inserter/distractors, and vice versa. That is, any load indicator described herein can be beneficially incorporated into other transport devices not specifically depicted.

In the example of FIGS. 11 and 12, a rotatable member (e.g., handle) 500 of a transport device 200A (e.g., screwdriver or reducer) is configured to couple with a shaft (not shown), via a coupler 520 such as an output connector. In particular cases, the coupler 520 is configured to connect with a drive shaft for loading a screw (e.g., screws 70, 90, 100, FIGS. 2-4). In particular implementations, the transport device 200A includes a load indicator 220A such as a torque cell 530. In certain cases, the load indicator 220A is axially aligned with, and located between, the rotatable member 500 and the shaft.

The load indicator 220A is shown with an outer housing 540 removed in FIG. 11, and with a housing 540 in place in FIG. 12. In certain cases, outer housing 540 can hermetically seal the load indicator 220A as described with reference to other implementations herein. In particular cases the torque cell 530 can be configured to measure a torque applied via the rotatable member 500 to the coupler 520 (and correspondingly, to the screw or other device being loaded). In certain cases, the torque cell 530 houses electronics such as communications equipment, connectors, and a power source. In certain cases, the power source is rechargeable.

In some aspects, the torque cell 530 is integrated in the handle 500, e.g., formed via an integral connection with the handle 500. In other cases, as noted herein, the torque cell 530 is removable from the handle 500. In certain cases, the coupler 520 is integral with the load indicator 220A (e.g., torque cell 530), and enables a tool-less connection with a transport device or actuator. In some cases, the tool-less connection provided by the coupler 520 includes a snap-to-couple or twist-to-couple connection with a transport device or actuator, for example, a transport device such as a screwdriver or reducer. In certain cases, an outer surface 560 of the coupler 520 includes at least one ridge or thread 570, e.g., near the distal end 580 of the coupler 520 for enabling snap-to-couple or twist-to-couple connection with a complementary connection feature on the transport device or actuator. In the example shown in FIGS. 11 and 12, at least two ridges 570 are shown for enabling snap-to-fit coupling with an output shaft, e.g., for driving a screw. In various implementations, the torque cell 530 is axially interposed between the handle 500 and the coupler 520.

Figure 14:
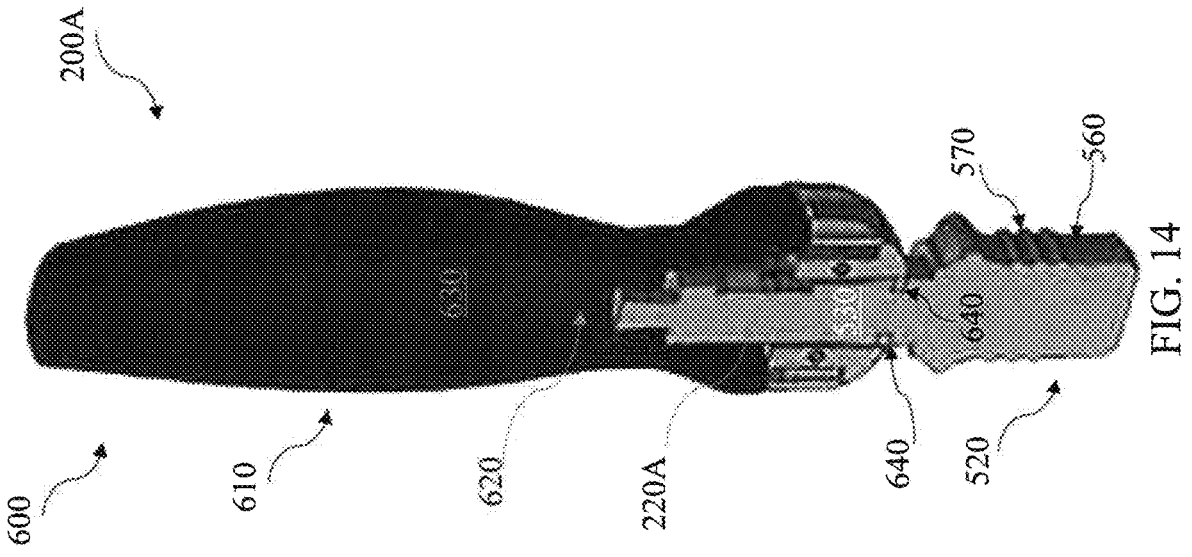
FIGS. 13 and 14 illustrate perspective views of a portion of a transport device including a load indicator according to various additional implementations.
Figure 13:
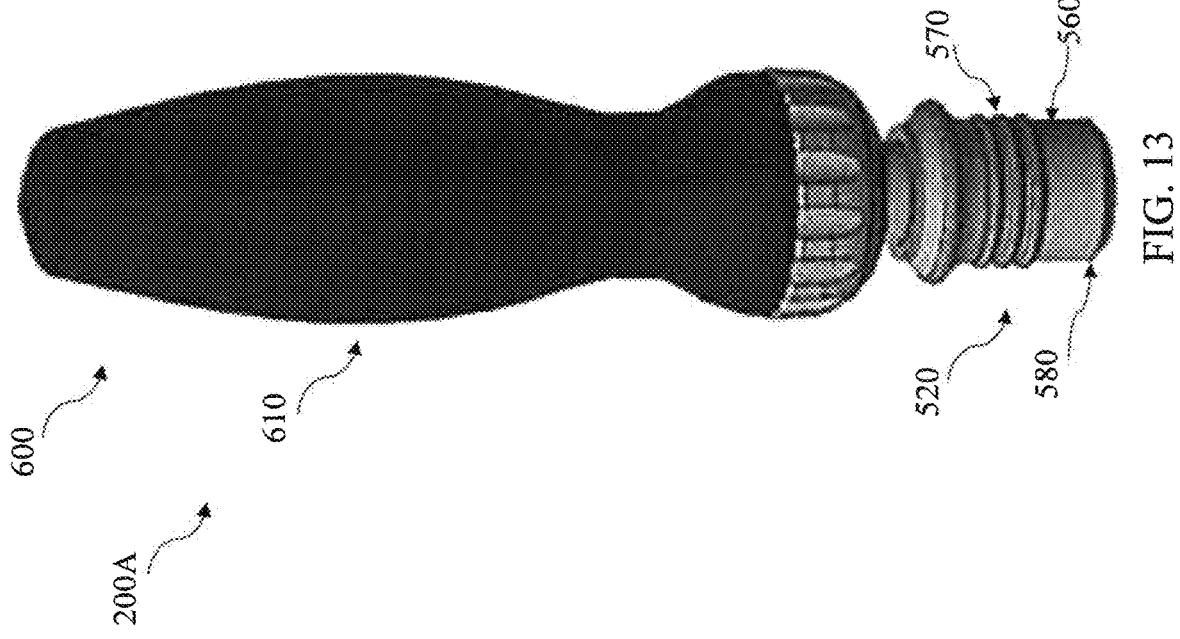

In still further implementations, as shown in FIGS. 13 and 14, another rotatable member 600 for a transport device 200A can include a handle 610 with an internal cavity 620 for housing at least a portion of a load indicator 220A (e.g., a torque cell 530). In these cases, the internal cavity 620 can be obstructed by the outer casing 630 of the handle 610, such that the torque cell 530 is at least partially enclosed by the handle 610. In a particular implementation, the torque cell 530 and related electronics and power source are sealed in the handle casing 630, e.g., via at least one seal 640. In some cases, the torque cell 530 is fixed to the handle casing 630. In additional implementations, the torque cell 530 can be removable from the casing 630. In certain of these cases, the torque cell 530 is connected with a coupler 520 as described herein, enabling, e.g., twist-to-fit or snap-to-fit connection with a shaft.

Figures 15, 16:
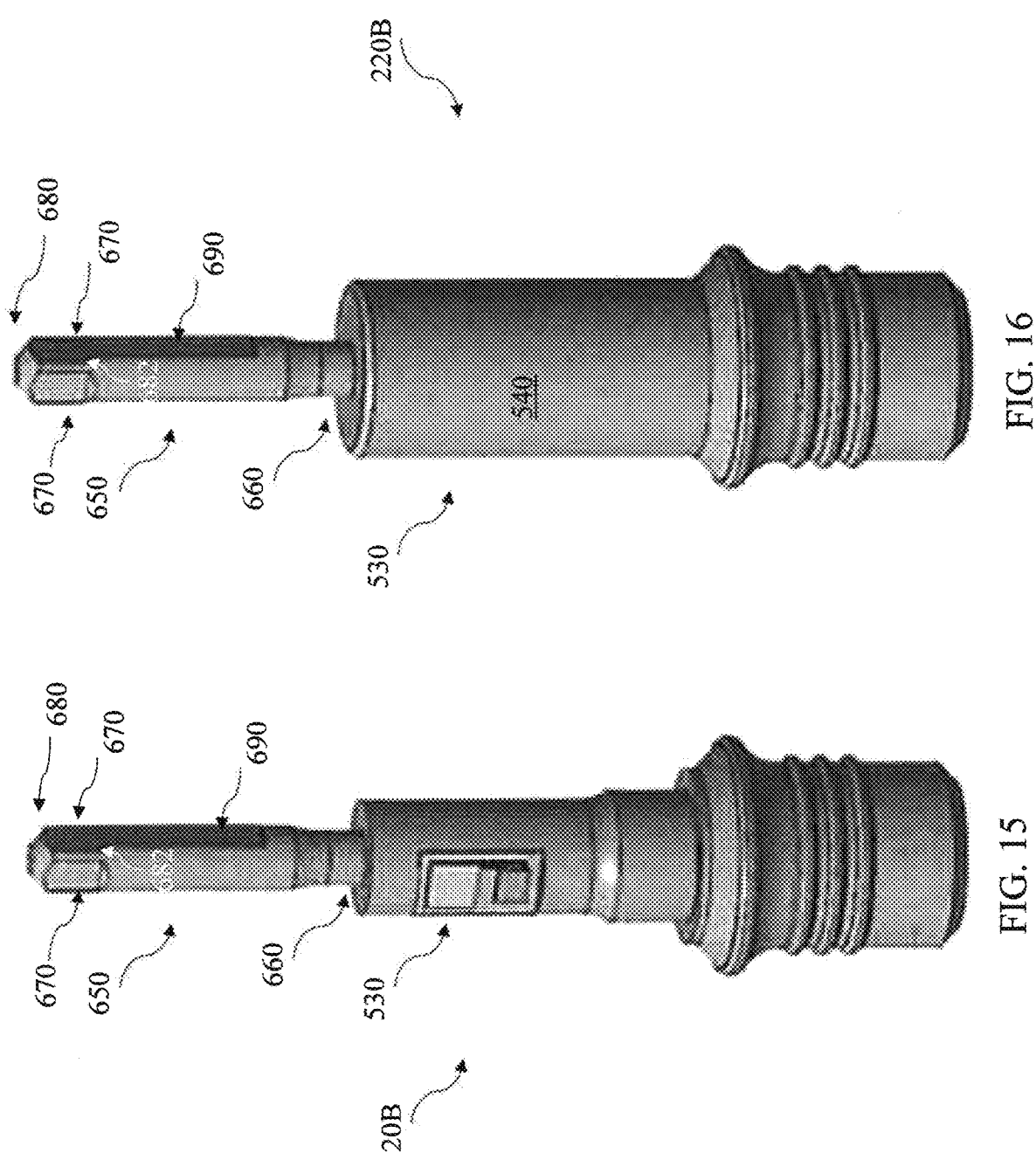
FIGS. 15 and 16 illustrate perspective views of a load indicator according to various implementations.

FIGS. 15 and 16 illustrate another implementation of a load indicator 220B that can be interchangeable with any other load indicator 220 described herein. In this cases, the load indicator 220B includes a connector 650 for enabling tool-less connection between a torque cell 530 and a handpiece such as a handle 500 (FIGS. 11 and 12), rotatable member 310 (e.g., FIGS. 5, 8, 9), and/or a power handpiece such as a power drill. In these cases, the connector 650 can extend from the proximal end 660 of the torque cell 530, and include a set of flat faces 670 at a proximal end 680 thereof. The flat faces 670 are separated by arcuate or angled sections 682 and enable mating with a complementary set of faces on the handle, rotatable member, or power handpiece. In certain cases, a slot 690 extends in the distal-proximal direction along at least one section of the connector 650 to allow the complementary coupler to engage the connector 650 axially.

Figures 17, 18:
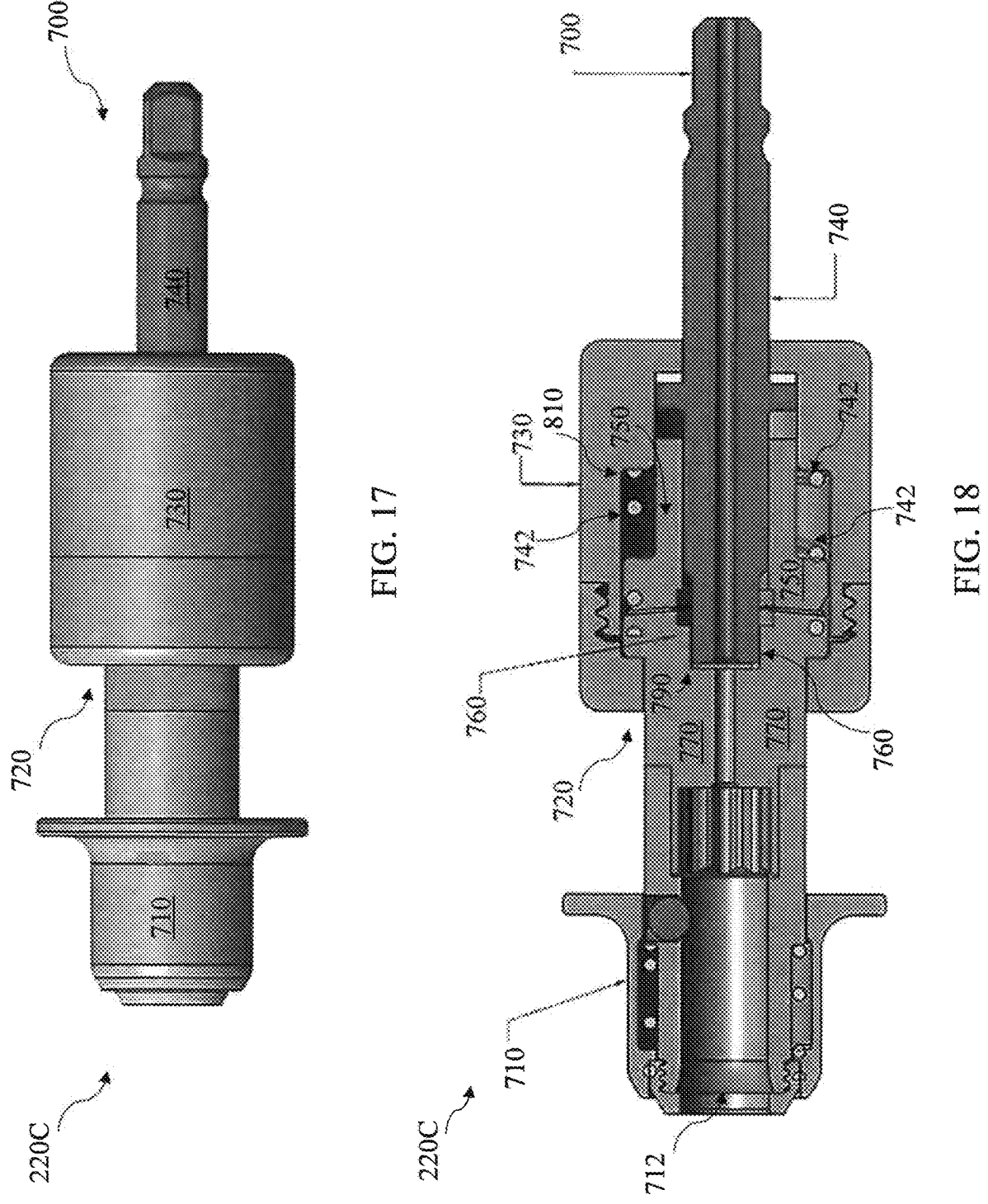
FIG. 17 is a perspective view of a load indicator according to various additional implementations.
FIG. 18 is a cross-section of the load indicator in FIG. 17.
Figure 19:
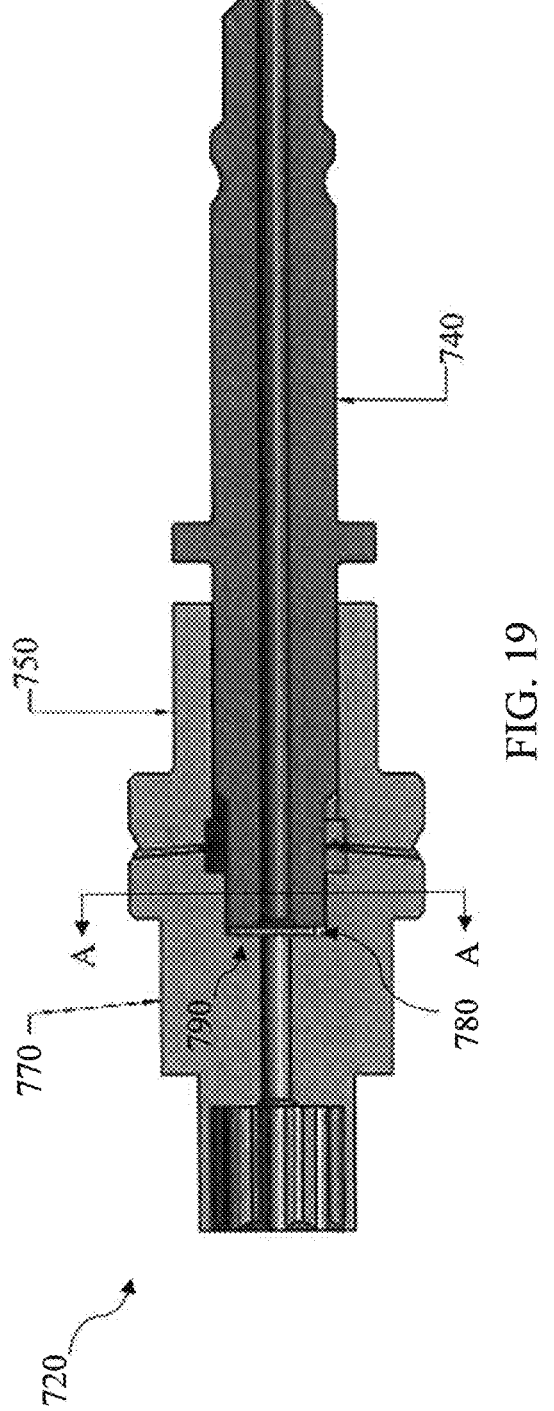
FIGS. 19 and 20 show distinct cross-sections of portions of the load indicator in FIGS. 17 and 18.
Figure 20:
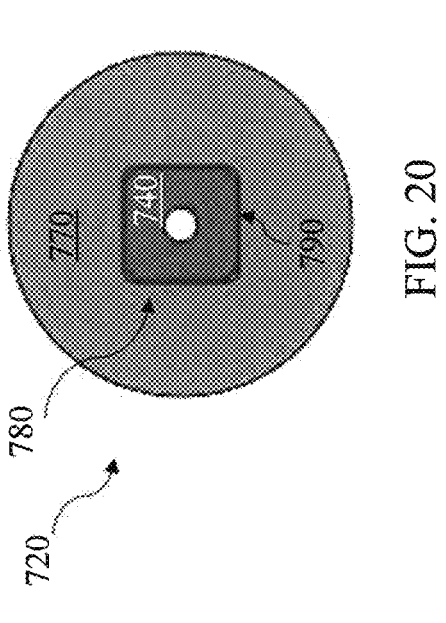
Figures 21, 22, 23:
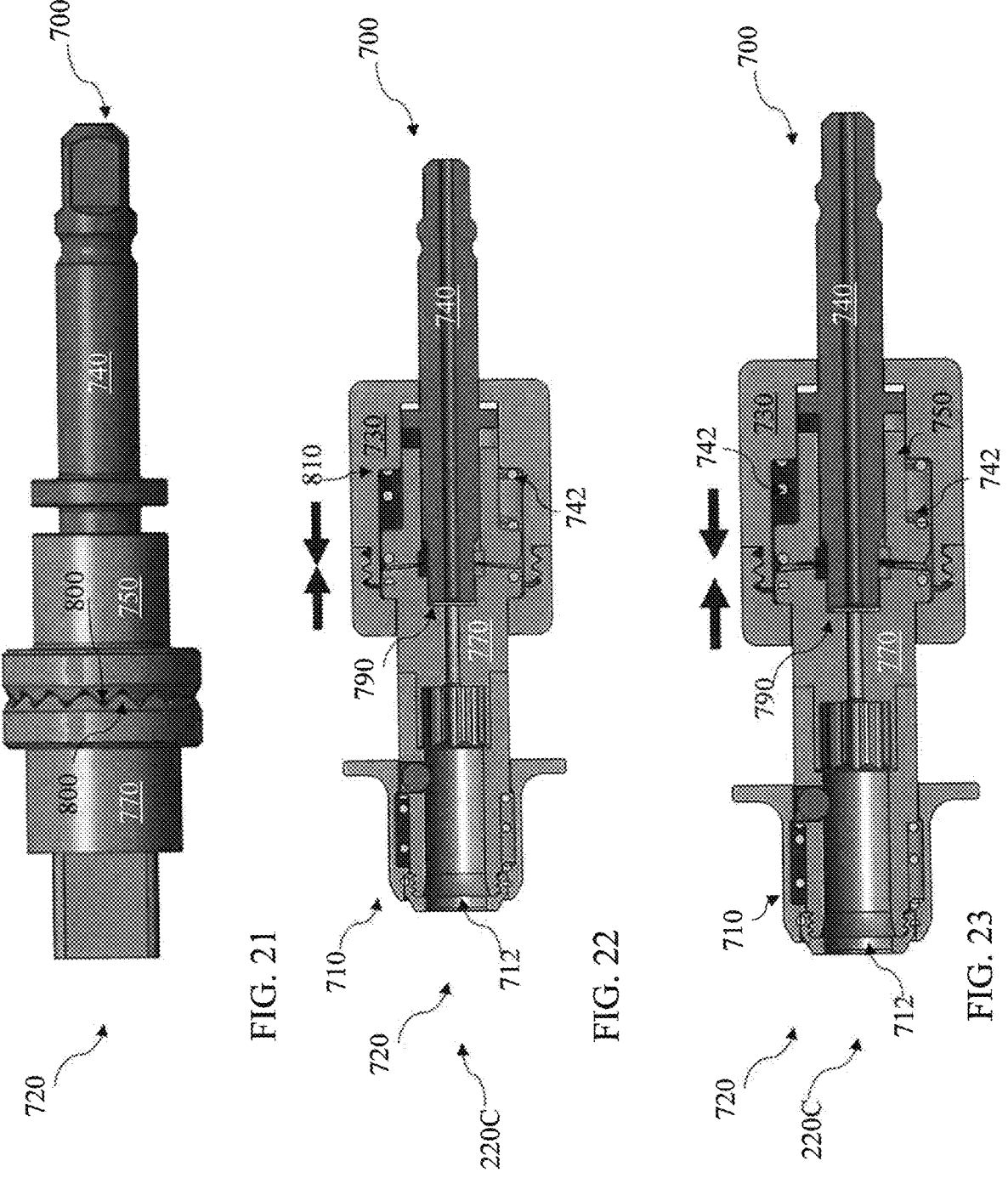
FIGS. 21-25 illustrate additional features of the load indicator in FIGS. 17-20 in perspective and cross-sectional views.
Figures 24, 25:
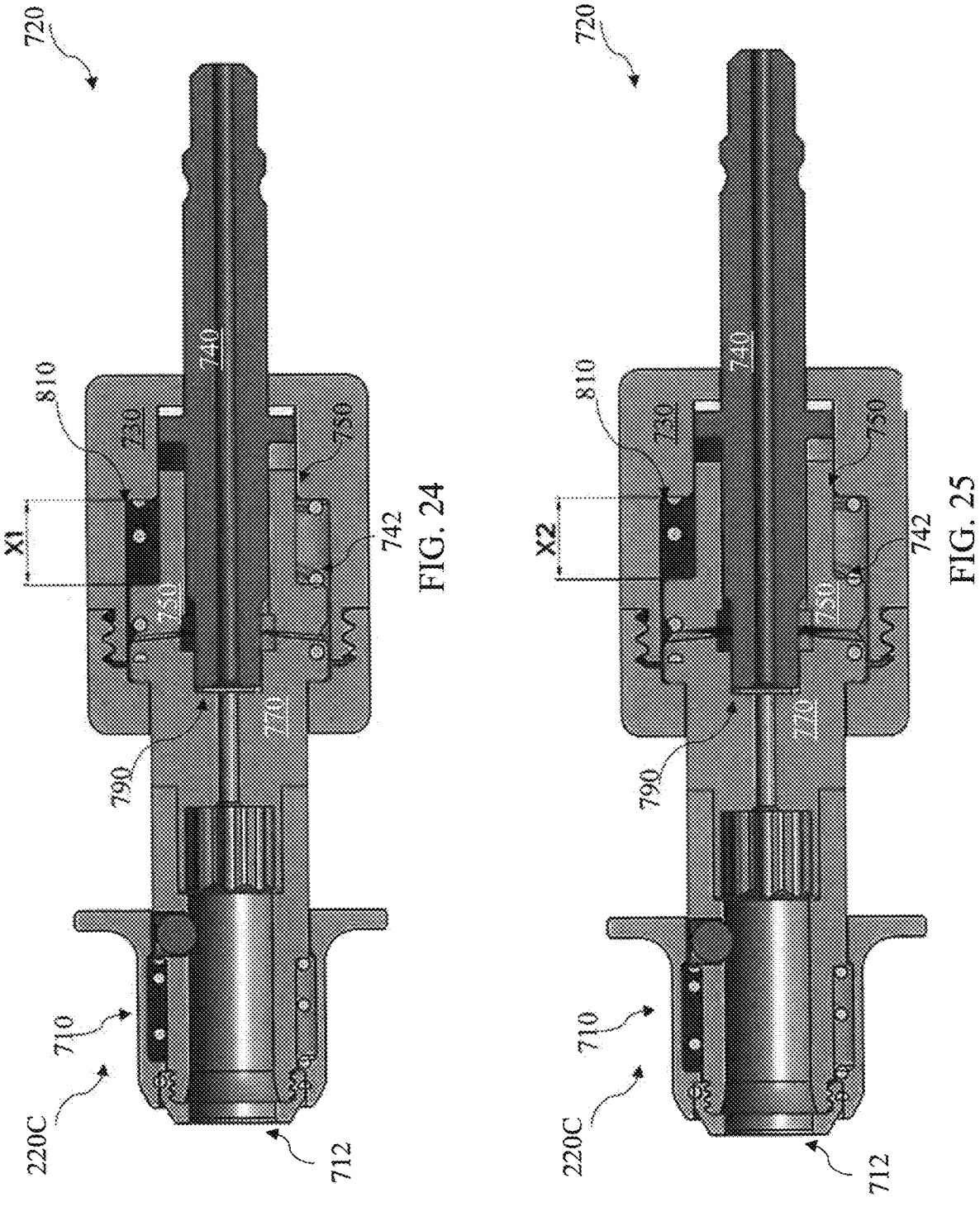

FIGS. 17 and 18 illustrate side, and cross-sectional views, respectively, of another type of load indicator 220C that can be interchangeable with any of the load indicators 220 described herein. In this case, the load indicator 220C includes a handle connector 700 that is configured to mate with a handle 500 (e.g., FIGS. 11-14), rotatable member 310 (e.g., FIGS. 5, 9, 10), and/or a power handpiece such as a power drill, and a drive shaft connector 710 that is configured to mate with a shaft for delivering an implant such as a screw or a spinal implant. In certain cases, the handle connector 700 includes a male connector component (e.g., similar to connector 650 in FIGS. 15 and 16) and the drive shaft connector 710 includes a female connector component having an internal slot 712 for receiving a portion of a drive shaft (e.g., a male portion of a drive shaft). In certain cases, the load indicator 220C includes a spring-loaded clutch mechanism 720 at least partially contained in an outer housing 730. The clutch mechanism 720 interfaces with a central driving shaft (or, input shaft) 740 that is connected with the rotatable member (e.g., handle) via the handle connector 700. A partial cross-section of the spring 742 is visible in FIG. 18. The driving (or, input) shaft 740 passes through a driven member 750 of the clutch mechanism 720 and into a recess 760 in a driving member 770 of the clutch mechanism 720. In some cases, as illustrated in the side cross-sectional view in FIG. 19 and a section taken along line A-A (FIG. 19) illustrated in FIG. 20, a distal end 780 of the shaft 740 has a keyed or interlocking shape such as a squared, triangular, rectangular, etc. shape that mates with a correspondingly keyed pocket 790 in the driving member 770. In the non-limiting example shown in FIG. 20, the distal end 780 of the shaft is squared, and mates with a square shaped pocket 790 in the driving member 770. In certain cases, the driven member 750 and driving member 770 of the clutch mechanism 720 have interlocking teeth 800 such that when the driving member 770 is rotated, it forces the driven member 750 to rotate in the same direction, e.g., as shown in the side view in FIG. 21. In some cases, the interlocking teeth 800 are angled such that the driven member 750 of the clutch separates from the driving member 770 when the clutch mechanism 720 is actuated. The spring 742 inside the clutch mechanism 720 forces the driven member 750 to remain in contact with the driving member 770 until the torque exerted on the driving member 770 overcomes the spring force of that spring 742. As such, the distance that the driven member 750 moves away from the driving member 770 is directly related to the spring force and the torque applied to the driving member 770. For example, FIG. 22 shows the clutch mechanism 720 fully engaged, signifying zero torque on the driving member 770. In comparison, FIG. 23 shows the clutch mechanism 720 partially separated, signifying some torque on the driving member 770. In various implementations, input torque can be determined by measuring the distance that the driven member 750 has moved with respect to the driving member 770. Input torque can also be determined by measuring the distance between the back or proximal end of the driven member 750 and the inner wall 810 of housing 730, for example, as shown in FIGS. 24 and 25. FIG. 24 shows an initial distance (X1) between the driven member 750 and the inner wall 810, signifying zero torque on the driving member 770. FIG. 25 shows a distinct distance (X2) between the driven member 750 and the inner wall 810, signifying some torque on the driving member 770.

Figure 26:
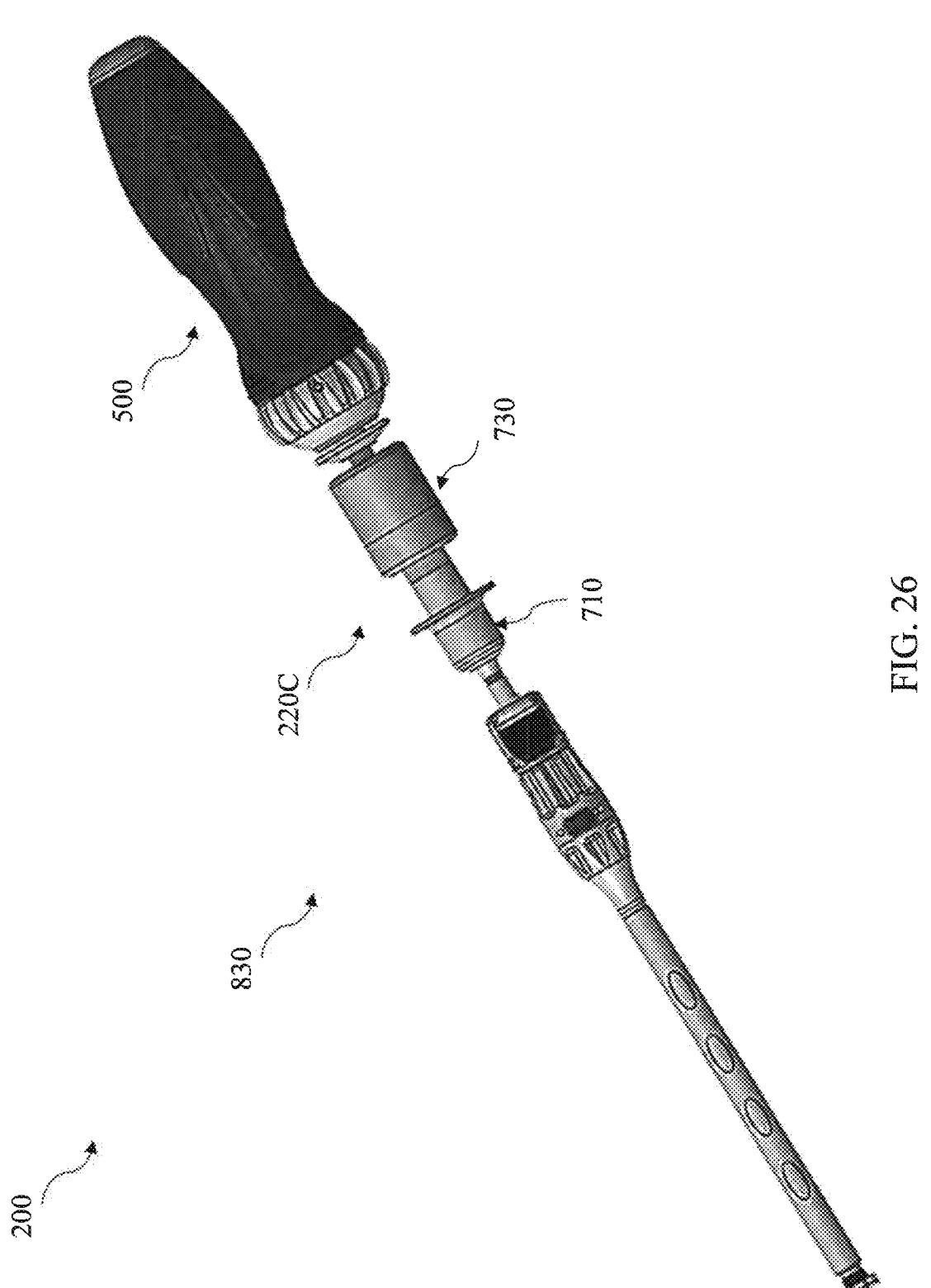
FIG. 26 illustrates a transport device including a load indicator according to one of various implementations.

As a further example, FIG. 26 shows a schematic view of a transport device 200 including a screwdriver 830 for delivering screws (e.g., screws 70, 90, 100, FIGS. 2-4) that employs the load indicator 220C. It is understood that the screwdriver 830 illustrated in FIG. 26 (or similar screw-driving instrument) can employ any of the load indicators 220 shown or described herein.

Figure 27:
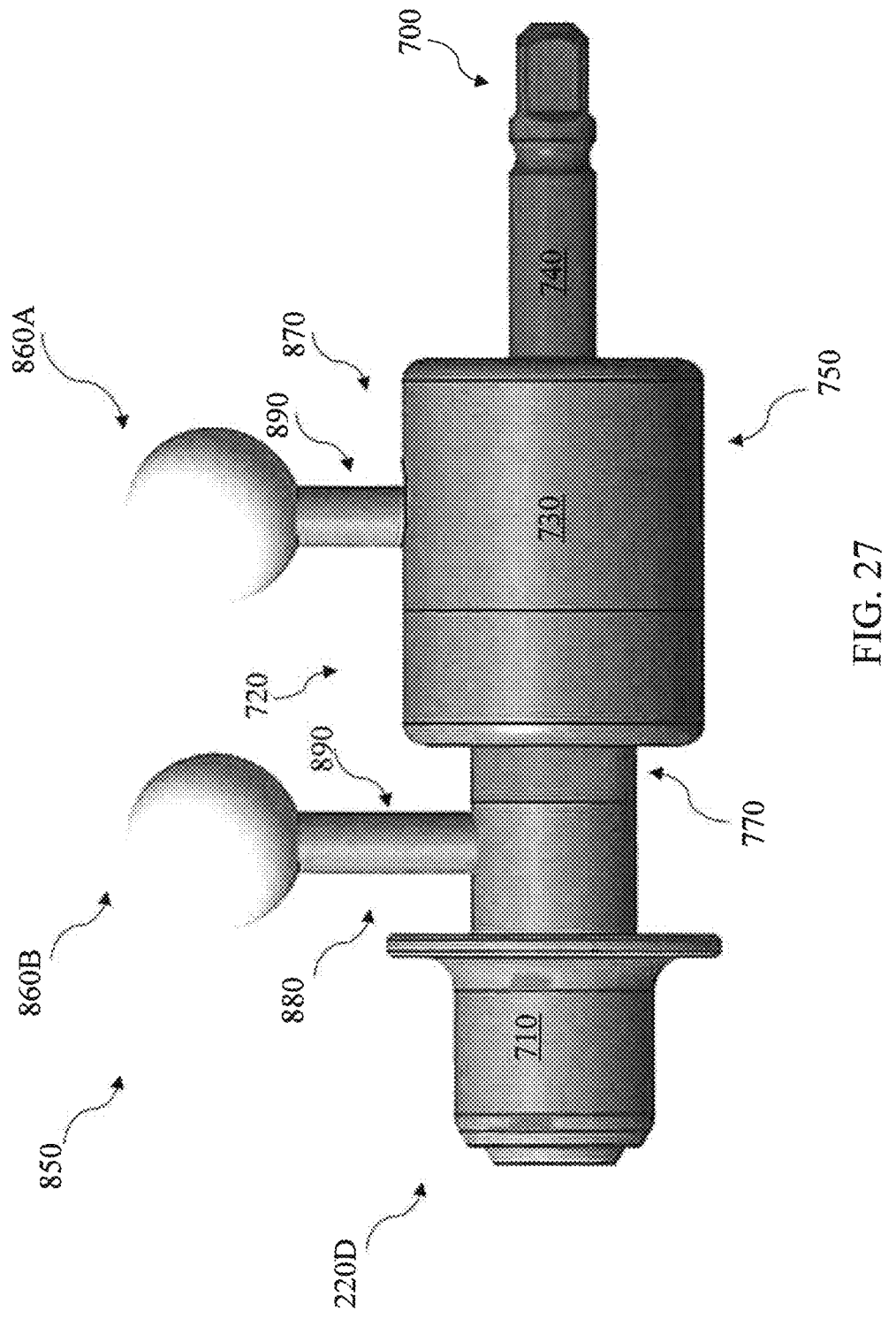
FIG. 27 illustrates a perspective view of a load indicator according to various additional implementations.

FIG. 27 illustrates, in side view, another implementation of a load indicator 220D according to various implementations. Load indicator 220D can be interchangeable with any of the load indicators 220 described herein. In these cases, the load indicator 220D can include an optical indicator cell 850 with at least two optical markers 860 (860A, 860B) on an exterior of the device, e.g., on a first portion 870 of the load indicator housing and a second portion 880 of the load indicator housing. In a particular implementation, the load indicator 220D is similar to the load indicator 220C in terms of internal components, but differs in that it includes optical markers 860 on the exterior of the device housing. In one example, an optical marker 860A is coupled to the driven member 750 of the clutch and a distinct optical marker 860B is coupled to a stationary portion of the load indicator 220D, e.g., via a coupler 890. With reference to FIGS. 22-26, in addition to FIG. 27, when torque is input to the drive (input) shaft 740, the members 750, 770 of the clutch separate and cause the distance between the optical markers 860A, 860B to change. In certain of these cases, the torque can be calculated based on the distance change between the optical markers 860A, 860B and the spring constant of the spring 742 in the clutch mechanism 720.

In certain cases, the optical markers 860 include at least one reflective infrared surface that is detectable by an optical tracking system such as an infrared camera. In a particular example, the optical markers 860 include infrared spheres or infrared discs, movement of which can be detected (e.g., tracked) by an infrared camera. In certain cases, the camera can be connected to a surgical management system including at least one computing device (e.g., including a processor and memory), such as described in U.S. Pat. No. 11,083,527 (previously incorporated by reference herein). In some aspects, the computing device is configured to record the location of the optical markers 860, calculate a distance change between the optical markers 860, and then calculate a torque value based on a distance change and a known value of the spring constant in the clutch mechanism 720. In other aspects, the optical markers 860 can be detected and/or tracked using an optical tracking system (e.g., one or more cameras such as a visible light camera) such as via stereophotogrammetry. In such cases, the optical markers 860 may vary based on at least one of shape, color, or pattern, e.g., optical marker 860A as a first shape, color and/or pattern and optical marker 860B as a second shape, color, and/or pattern. The optical tracking system can be configured to detect the distinction between the markers 860A, 860B, and track relative movement and/or position of those markers 860A, 860B. As described relative to the reflective marker cases, the computing device is configured to record the location of the optical markers 860 as detected via stereophotogrammetry, calculate a distance change between the optical markers 860, and then calculate a torque value based on a distance change and a known value of the spring constant in the clutch mechanism 720.

Figure 28:
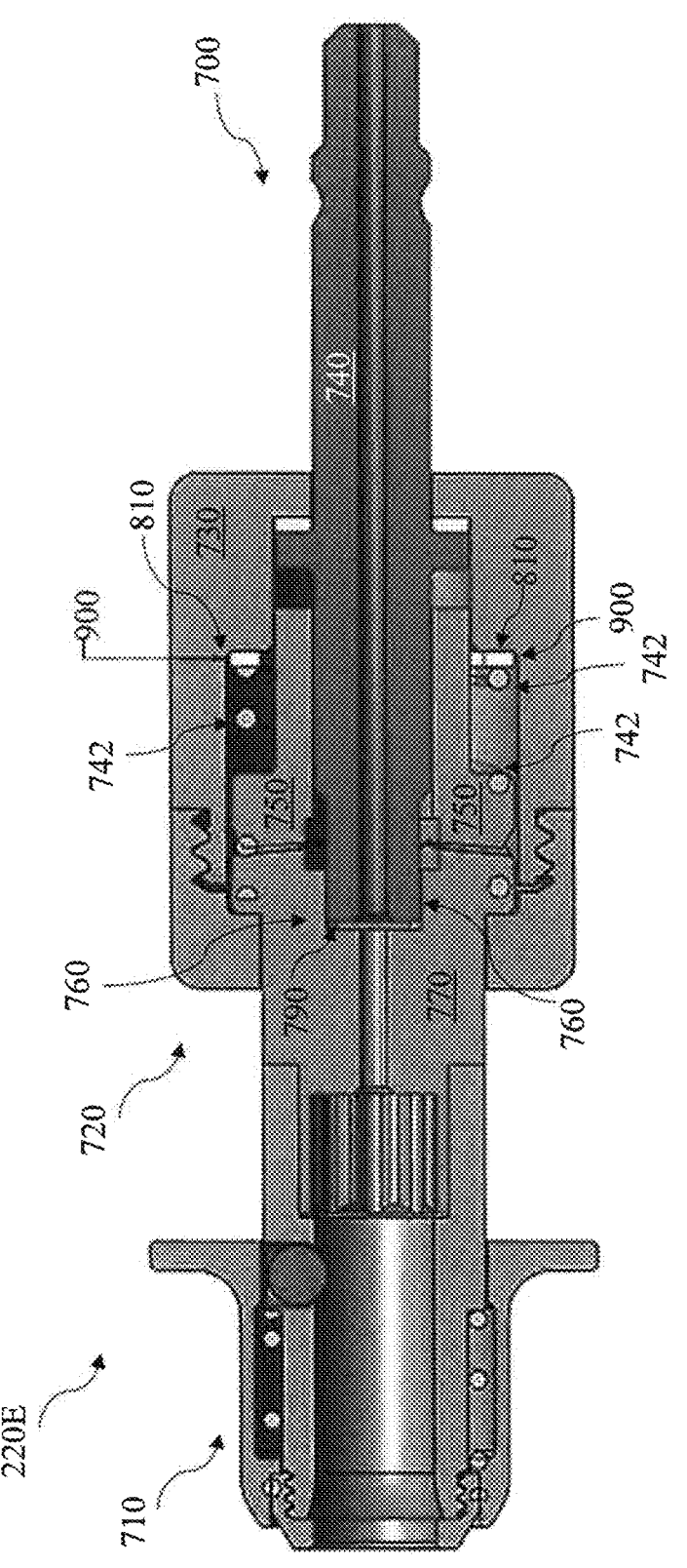
FIG. 28 illustrates a cross-sectional view of a load indicator according to various additional implementations.

FIG. 28 illustrates, in cross-sectional view, another implementation of a load indicator 220E according to various implementations. Load indicator 220E can be interchangeable with any of the load indicators 220 described herein. In these cases, the load indicator 220E can include a handle connector 700, drive shaft connector 710, and clutch mechanism 720 similar to the load indicators 220C, 220D described with reference to FIGS. 17-27. In contrast to those previously described load indicators, load indicator 220E can include a force sensor 900, such as an internal force sensor. In particular implementations, the force sensor 900 is located on the inner wall 810 of housing 730. In these implementations, the force sensor 900 is positioned to detect a change in force applied to the housing 730 when the clutch mechanism 720 moves, e.g., when the driven member 750 moves relative to the driving member 770. In some examples, the force sensor 900 is positioned against the spring 742 such that the force sensor 900 reacts to the change in spring force that occurs when the driven member 750 and driving member 770 separate as a result of input torque. In certain examples, the force sensor 900 includes a force-sensitive resistor, a piezoelectric sensor, a potentiometer, or any other sensor that exhibits or detects change in resistance, voltage, or capacitance based on a force. In certain cases, multiple force sensors 900 are positioned on the inner wall 810. In various implementations, the force sensor 900 is coupled with a circuit board (e.g., onboard the load indicator 220E or proximate the load indicator 220E in the apparatus) that outputs serial readings of resistance, voltage, or capacitance. In some cases, these serial readings are converted to input torque and the input torque value is recorded and/or output (via visual, audible, etc. feedback), e.g., by a surgical management system such as those described herein. In further implementations, components of the surgical management system such as an electronics package are located at the load indicator 220E. In other cases, the electronics package is remote from the load indicator 220E.

Figure 29:
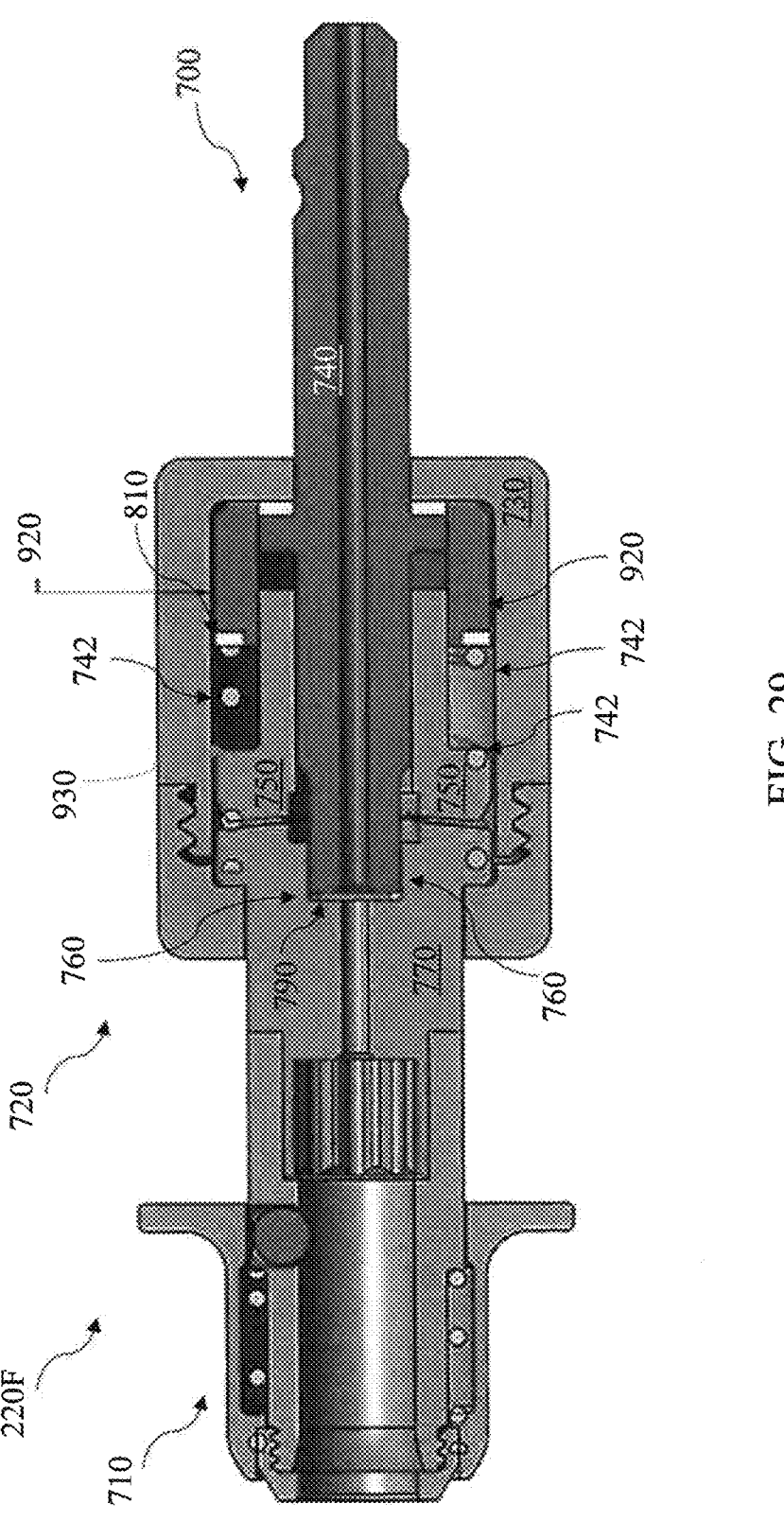
FIG. 29 illustrates a cross-sectional view of a load indicator according to various additional implementations.

FIG. 29 illustrates, in cross-sectional view, another implementation of a load indicator 220F according to various implementations. Load indicator 220F can be interchangeable with any of the load indicators 220 described herein. In these cases, the load indicator 220F can include a handle connector 700, drive shaft connector 710, and clutch mechanism 720 similar to the load indicators 220C, 220D, 220E described with reference to FIGS. 17-28. In contrast to those load indicators, load indicator 220F can include a proximity sensor 920, such as an internal proximity sensor. In particular implementations, the proximity sensor 920 is located on the inner wall 810 of housing 730. In some examples, the proximity sensor 920 faces a rear (or, back or proximal) surface 930 of the driven member 750. In these cases, similarly to load indicator 220E, the input torque can be related to the position of the driven member 750 (e.g., as detected by proximity sensor 920) such that proximity changes based on applied torque. In various implementations, the system relates the position of the rear surface 930 of the driven member 750 to the applied torque, e.g., based on a known value of the spring constant. In some cases, the proximity sensor 920 includes one or more of an inductive sensor, an ultrasonic sensor, a capacitive sensor, a magnetic sensor, or an optical sensor. Specific example sensors can include a hall effect sensor, an ultrasonic sensor, or a potentiometer. The output of the sensor 920 can change based on the proximity of the driven member 750 (e.g., rear surface 930), which as noted herein, moves in response to applied torque. In some cases, the proximity sensor 920 is coupled with a circuit board (e.g., onboard the load indicator 220F or proximate the load indicator 220F in the apparatus) that outputs serial readings of resistance, voltage, or capacitance. In some cases, these serial readings are converted to input torque and the input torque value is recorded and/or output (via visual, audible, etc. feedback), e.g., by a surgical management system such as those described herein. In further implementations, components of the surgical management system such as an electronics package are located at the load indicator 220F. In other cases, the electronics package is remote from the load indicator 220F.

Figures 30, 31:
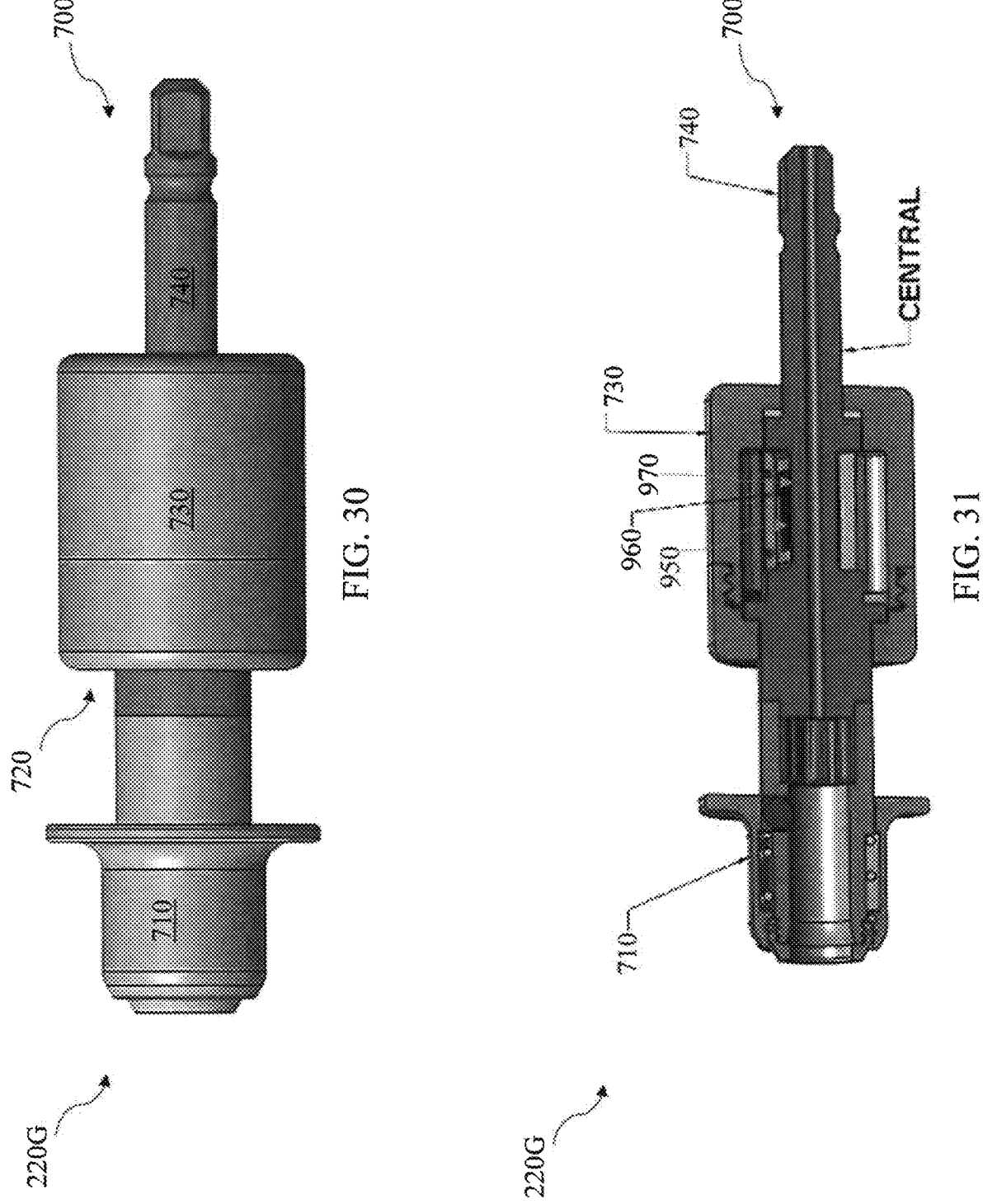
FIGS. 30 and 31 illustrate perspective and cross-sectional views, respectively, of a load indicator according to various additional implementations.
Figure 32:
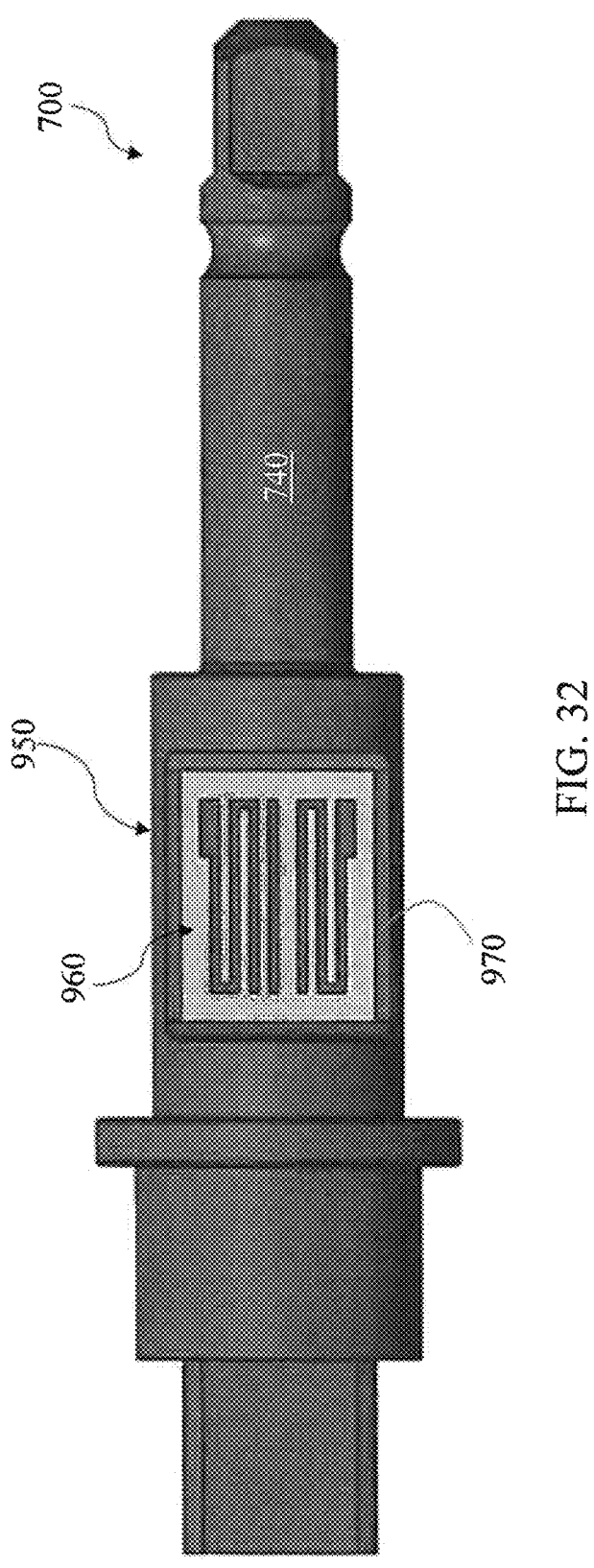
FIG. 32 shows a portion of the load indicator from FIGS. 30 and 31.

FIGS. 30 and 31 illustrate, in side perspective and cross-sectional views, respectively, another implementation of a load indicator 220G according to various implementations. Load indicator 220G can be interchangeable with any of the load indicators 220 described herein. In these cases, the load indicator 220G can include a handle connector 700, drive shaft connector 710, and in some cases, a clutch mechanism 720 similar to the load indicators 220C-F described with reference to FIGS. 17-29. In contrast to those load indicators, the drive shaft 740 can include a recess (or slot or cutout) 950 in the portion within housing 730. The recess 950 creates a beam along the drive shaft 740, and in various implementations, a strain gauge 960 is located on an approximately planar surface 970 of the cutout 950. FIG. 32 shows a partial view of the shaft 740 with a recess 950 creating an approximately planar surface 970, and a strain gauge 960 located on the surface 970. In certain cases, the strain gauge 960 is coupled with a circuit board and/or additional electronics for detecting a reading from the gauge 960, and in some cases, relaying that reading to a surgical management system as described herein. In various implementations, the system relates the strain on the drive shaft 740 as measured by the strain gauge 960 with a torque on the implant. In a particular case, the strain gauge 960 detects strain on the surface of the shaft 740 (e.g., along surface 970) caused by torque acting on the shaft 740. When torque is transmitted through the shaft 740, the resistance across the strain gauge 960 changes. That change in resistance causes a change in voltage across the connected circuit, which can be detected by a circuit board or additional electronics. In some cases, serial readings are converted to input torque and the input torque value is recorded and/or output (via visual, audible, etc. feedback), e.g., by a surgical management system such as those described herein. In further implementations, components of the surgical management system such as an electronics package are located at the load indicator 220G. In other cases, the electronics package is remote from the load indicator 220G.

Figure 33:
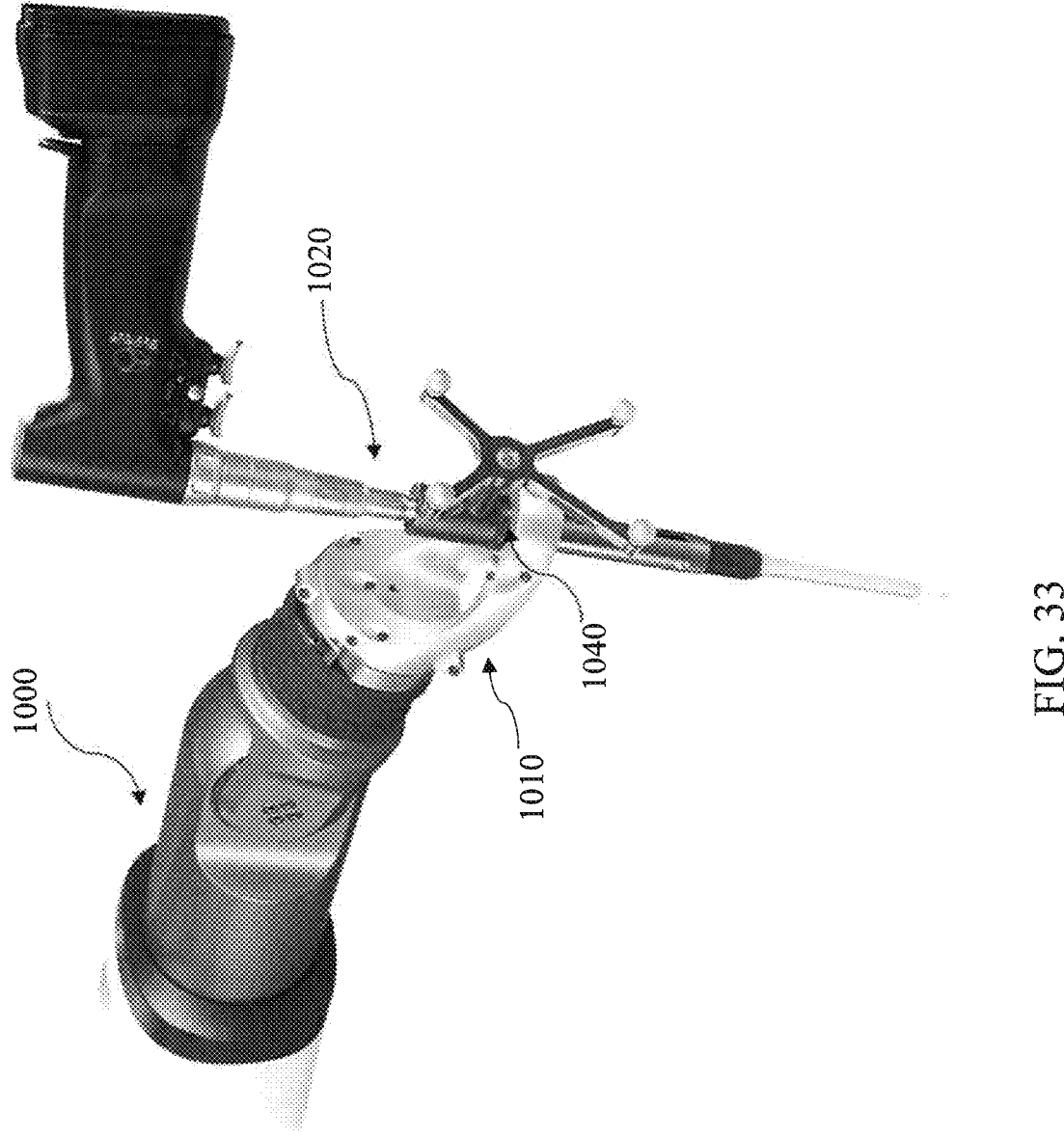
FIG. 33 shows an example of a robotic arm interfacing with a transport device according to various implementations.

FIG. 33 illustrates a load indicator according to various additional implementations. In this depiction, a robotic arm 1000 is shown including an end effector 1010 for retaining a transport device 1020. In some cases, the transport device 1020 includes a handpiece such as a power screwdriver, however, it is understood that the end effector 1010 can be configured to retain any apparatus described herein, e.g., any transport device described herein. The end effector 1010 enables the robotic arm 1000 to guide the transport device 1020 and control precise delivery, removal, or manipulation of an implant such as an intervertebral spacer, screw, etc. In certain implementations, the end effector 1010 includes a load indicator 1040, illustrated in schematic cross-section in FIG. 34. In this case, the end effector 1010 includes a guide (or guide tube) 1050 that enables the medical professional (e.g., surgeon) to move the transport device 1020, and also includes the load indicator 1040, including a key and slot mechanism 1060 that enables torque measurement of the inserted instrument (e.g., transport device 1020). In these cases, the transport device 1020 includes a protrusion 1070 along an outer surface thereof, and the guide 1050 includes a corresponding slot 1080 that accepts (mates with) the protrusion 1070. In certain cases, a sleeve (not shown) for receiving the transport device 1020 also includes a slot that enables the transport device to pass axially therethrough and engage with the slot 1080 in the guide 1050. In these cases, when the user applies torque on the transport device 1020, the protrusion 1070 interfaces with guide 1050 (at slot 1080) and applies torque to the end effector 1010. As shown in FIG. 34, the guide 1050 can include an offset cam, or slot 1080 configured to receive the protrusion 1070. When torque (shown as (T)) is applied to the guide 1050, the cam including slot 1080 rotates around central axis (A), such that the cam profile applies a force to a load indicator 1040 such as a load cell. The load indicator 1040 can include any load cell described herein, and can include or be coupled with additional electronics such as a detection circuit and/or computing device(s).

In additional implementations, the transport device 1020 shown in FIG. 33 can include an integrated load indicator such as any of the load indicators described herein (e.g., load indicator(s) 220). In some cases, the transport device 1020 includes a handpiece such as a power screwdriver, and can be configured to communicate with any of the surgical management systems described herein, e.g., as described in U.S. Pat. No. 11,083,527 (previously incorporated by reference herein). In certain implementations, the handpiece can include a torque sensing motor that includes one or more strain gauges. In such cases, strain gauges are coupled to load-bearing components such as the motor shaft or other components that are prone to deformation under torque. As torque is applied, the strain gauges detect mechanical strain and change their electrical resistance accordingly. That change in resistance is proportional to the applied torque, which can be detected and measured according to approaches described herein. For example, a circuit and/or computing device can be configured to condition a signal received from the strain gauge to detect a change in resistance, and correlate that resistance change with a torque value. In particular cases, the circuit and/or computing device relying on use of the strain gauge-based load indicator (e.g., on the motor) runs an algorithm (or is otherwise calibrated) to account for additional data inputs about the condition of the motor to calculate torque. For example, data inputs such as temperature (or temperature variation) and sensor nonlinearity can adjust the calculation of torque from the resistance change. In particular cases, the motor controller is configured to modify the motor driver based on the detected torque, e.g., based on a comparison of the detected torque with a threshold or range of desired torque value(s). In such cases, the motor controller dynamically adjusts at least one motor driver parameter (e.g., power, speed, etc.) based on the detected torque value as calculated from the strain gauge.

As noted herein, one or more of the load indicators (e.g., load indicators 220, or load indicator 1040) can be applied to transport devices not specifically depicted or described. For example, rod reducers, removal tools, etc., can benefit from the load indicators and disclosed approaches of the various implementations. Additional transport devices such as rod reducers are disclosed in U.S. Pat. No. 10,136,927, and further transport devices such as fixation instruments (e.g., guides and guide tubes, are provided in US Patent Application Publication Nos. 2020/0297393 (U.S. application Ser. No. 16/898,713) and 2021/0085485 (U.S. application Ser. No. 16/995,602), each of which is incorporated by reference in its entirety. Further, any handpiece can benefit from the use of load indicators described herein, for example, handpieces with a central drive shaft can incorporate any of the load indicators 220 disclosed herein. While various specific load indicators are disclosed, it is understood that the load indicators in transport devices can include at least one of: a load cell, a torque cell, an active marker cell, an optical indicator cell, a proximity indicator cell, or a strain gauge. Additional examples of load indicators can include a pressure-sensitive film, or a capacitive sensor.

Further, as noted herein, load indicators can include or otherwise be coupled with electronics, which can be configured to communicate (e.g., wirelessly and/or hard-wired connection) with a remote surgical management system. In some cases, the electronics include or are coupled with the load indicator, a power source, and signal conditioning electronics such as an interface circuit to process and output a signal. In certain cases, the interface circuit includes a signal processor such as a digital signal processor (DSP), a logic engine to filter/condition the signal, and a controller to control onboard functions such as displays and transmission of signals to external components such as an external receiver. Additionally, the load indicators can provide feedback to a medical professional (e.g., surgeon) during and/or after a procedure via the surgical management system.

In particular implementations, the surgical management system includes a feedback system that has a controller (e.g., one or more microcontrollers) with least one processing unit, or processor (PU) (such as one or more microprocessors) coupled with or containing a memory (e.g., including one or more storage components such as memory chips and/or chipsets). The memory stores instructions (e.g., load calculation and/or feedback instructions) which when executed by the PU(s) cause the PU to: i) compare the load data obtained from the load indicator with a load threshold for the transport device; and ii) provide an indicator that the load data satisfies or does not satisfy the load threshold for the transport device. In particular cases, the load threshold includes a load range for the transport device that is indicative of a desired loading of the implant (e.g., intervertebral implant, screw, etc.). In various implementations, the load threshold includes a range with an upper and lower bound, which can account for some variation in measurement based on a known measurement margin of error, e.g., of the load indicator. In additional implementations, the load threshold includes a load value that accounts for a known measurement error, e.g., by one, two, or three percent. In certain implementations, the load threshold is based at least in part on a model that correlates clinical data representing patient-specific bone quality with implant characteristics, e.g., screw pullout. This clinical data can be engrained in a model stored in the feedback instructions, and can be updatable, e.g., as further data becomes available.

In particular implementations, the load data at least partially represents an amount of torque applied to a transport device during loading, e.g., inserting of an intervertebral implant or tightening of the lock screw within a pedicle screw receiver and a compressive force applied to the transport device. In certain of these cases, e.g., where the load data does not satisfy the load threshold, the indicator can include an indicator of an amount that the torque applied to the implant should be modified to satisfy the load threshold for the transport device.

Devices such as transport devices, end effectors, and/or other handpieces described herein are described as including communication devices and related electronics. These communications device(s) can include one or more transmitters and/or receivers (e.g., wireless and/or hard-wired transmitters/receivers). In various implementations, the communication devices are configured for a plurality of communication protocols, e.g., wireless protocols such as Wi-Fi, Bluetooth, BLE, Zigbee, etc., as well as radio communication and intercom communications, and/or a hardwired connection (e.g., fiber optic connection).

The transport devices described herein can also be coupled with a navigation system in order to provide navigation information about a position of instruments. For example, the navigation system can include an optical tracking system such as a camera or laser-based tracking system, a Global Positioning System (GPS), an inertial measurement unit (IMU), etc. In certain cases, the navigation system is configured to determine a distance moved by the instrument when the instrument changes position, which the navigation system communicates to the feedback system. One or more components of a navigation system can be located within or otherwise integrated with a housing that is mounted to or otherwise coupled with one or more of the transport device(s). The feedback system can also be configured to provide post-operative data and analysis of a procedure and/or device usage, e.g., to enhance future procedures and/or diagnose inefficiencies in a past procedure. In certain implementations, the feedback system is configured to update transport device instructions based on identified inefficiencies or errors in transport device sequencing and/or device usage during a given procedure. In particular implementations, the feedback system includes a logic engine configured to modify transport device instructions iteratively, e.g., on a procedure-by-procedure basis.

As noted herein, the implant feedback apparatuses, systems and methods disclosed according to various implementations provide numerous benefits relative to conventional implant apparatuses and systems. For example, the disclosed apparatuses, systems, and methods can enhance efficacy of spinal fixation procedures, as well as mitigate operator (e.g., surgeon) error in performing such procedures. Various disclosed implementations can improve patient outcomes when compared with conventional spinal fixation procedures. Additionally, the disclosed implementations can provide real-time and/or post-operative feedback on implant loading, enhancing both current procedural outcomes as well as future surgical outcomes. In certain implementations, the feedback apparatuses can provide information to an operator regarding desired implant loading, thereby mitigating or avoiding overloading of implants and/or instruments at any given time during the procedure.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

While inventive features described herein have been described in terms of preferred embodiments for achieving the objectives, it will be appreciated by those skilled in the art that variations may be accomplished in view of these teachings without deviating from the spirit or scope of the invention. Also, while this invention has been described according to a preferred use in spinal applications, it will be appreciated that it may be applied to various other uses desiring surgical fixation, for example, the fixation of long bones.

A number of implementations have been described. Nevertheless, it will be understood that additional modifications may be made without departing from the scope of the inventive concepts described herein, and, accordingly, other implementations are within the scope of the following claims.

We claim:

1. An apparatus for providing feedback on an implant, the apparatus comprising:

a transport device for loading the implant in a patient;

an actuator coupled with the transport device for actuating movement of the implant in the patient; and a load indicator coupled with at least one of the actuator or the transport device, the load indicator providing feedback indicative of a load on at least one of the implant or a body part of the patient wherein the load indicator includes a housing containing a communications device for transmitting the feedback indicative of the load to a surgical management system, wherein the load indicator includes an optical indicator cell with at least two optical markers, wherein the transport device includes a clutch mechanism, and the at least one of the two optical markers is coupled to a movable portion of the clutch mechanism an the at least one of the two optical markers if coupled to a stationary portion of the clutch mechanism, wherein the load indicator calculates a torque based on a distance change between the at least two optical markers as the transport device and a spring constant of a spring position in the clutch mechanism, as the transport device is operated.

2. The apparatus of claim 1, wherein the transport device comprises an intervertebral body (IB) transport device.

3. The apparatus of claim 2, wherein the implant comprises an intervertebral spacer for occupying an intervertebral disc space in a spinal region of the patient, and wherein the intervertebral body (IB) transport device comprises:

a guide body;

a distractor coupled with the guide body for transporting the intervertebral spacer relative to the intervertebral disc space; and set of distraction arms for positioning the intervertebral spacer in the intervertebral disc space.

4. The apparatus of claim 3, wherein the actuator comprises a driver coupled with a distal end of the distractor for causing movement of the distractor relative to the guide body.

5. The apparatus of claim 4, wherein the driver is directly coupled with the load indicator, and wherein the driver comprises a rotatable member, wherein the set of distraction arms are configured to expand to engage one or more vertebra adjacent the intervertebral disc space in response to rotation of the rotatable member, and wherein in response to rotation of the rotatable member after the distraction arms engage the one or more vertebra adjacent the intervertebral disc space, the distractor transports the intervertebral spacer relative to the intervertebral disc space.

6. The apparatus of claim 4, wherein the markers are configured to provide visual feedback of an amount of rotation of the driver, and wherein the housing is configured to be hermetically sealed and includes a rechargeable power source.

7. The apparatus of claim 1, wherein the load indicator is disposable and configured for one-time use.

8. The apparatus of claim 1, further comprising a release mechanism for releasing the implant from the transport device, wherein the release mechanism is adjustable independently of the actuator.

9. The apparatus of claim 1, wherein the transport device comprises a screwdriver for loading a screw into the body part of a patient or into an implant in a patient, the screwdriver having:

a rotatable member for driving the screw;

a shaft extending from the rotatable member; and the load indicator coupled with at least one of the rotatable member or the shaft.

10. The apparatus of claim 9, wherein the load indicator is axially aligned with, and located between, the rotatable member and the shaft.

11. The apparatus of claim 9, wherein the load indicator is housed within the rotatable member.

12. The apparatus of claim 1, further comprising at least one coupler integral with the load indicator, the at least one coupler enabling a snap-to-couple or twist-to-couple connection with one or both of the transport device or the actuator.

13. A system for providing feedback from an implant comprising:

an apparatus for providing feedback on an implant, the apparatus comprising:

a transport device for loading the implant in a patient;

an actuator coupled with the transport device for actuating movement of the implant in the patient; and a load indicator coupled with at least one of the actuator or the transport device, the load indicator providing feedback indicative of a load on at least one of the implant or a body part of the patient; and an optical feedback system for detecting at least one additional indicator of the load on at least one of the implant or the body part of the patient, wherein the load indicator includes a housing containing a communications device for transmitting the feedback indicative of the load to a surgical management system, wherein the load indicator includes an optical indicator cell with at least two optical markers, wherein the transport device includes a clutch mechanism, and the at least one of the two optical markers is coupled to a movable portion of the clutch mechanism an the at least one of the two optical markers if coupled to a stationary portion of the clutch mechanism, wherein the load indicator calculates a torque based on a distance change between the at least two optical markers as the transport device and a spring constant of a spring position in the clutch mechanism, as the transport device is operated.

14. A method of performing an anterior lumbar interbody fusion (ALIF) or a lateral lumbar interbody fusion (LLIF) procedure using the apparatus of claim 1.

* * * * *